(12) United States Patent
Zhang et al.

(10) Patent No.: US 12,369,803 B2
(45) Date of Patent: Jul. 29, 2025

(54) HEART RATE DETECTION METHOD AND ELECTRONIC DEVICE

(71) Applicant: Beijing Honor Device Co., Ltd., Beijing (CN)

(72) Inventors: Xiaowu Zhang, Shenzhen (CN); Danhong Li, Shenzhen (CN); Haoxuan Di, Shenzhen (CN)

(73) Assignee: Beijing Honor Device Co., Ltd., Beijing (CN)

( * ) Notice: Subject to any disclaimer, the term of this patent is extended or adjusted under 35 U.S.C. 154(b) by 0 days.

(21) Appl. No.: 18/017,935

(22) PCT Filed: Aug. 30, 2022

(86) PCT No.: PCT/CN2022/115913
§ 371 (c)(1),
(2) Date: Jan. 25, 2023

(87) PCT Pub. No.: WO2023/071501
PCT Pub. Date: May 4, 2023

(65) Prior Publication Data
US 2024/0252052 A1    Aug. 1, 2024

(30) Foreign Application Priority Data

Nov. 1, 2021  (CN) .......... 202111284126.2
Dec. 29, 2021  (CN) .......... 202111644631.3

(51) Int. Cl.
A61B 5/024 (2006.01)
A61B 5/00 (2006.01)

(52) U.S. Cl.
CPC .......... *A61B 5/02416* (2013.01); *A61B 5/681* (2013.01); *A61B 5/7267* (2013.01); *A61B 5/742* (2013.01)

(58) Field of Classification Search
CPC ... A61B 5/02416; A61B 5/681; A61B 5/7267; A61B 5/742; A61B 5/7203
See application file for complete search history.

(56) References Cited

U.S. PATENT DOCUMENTS

| | | |
|---|---|---|
| 2014/0275854 A1 | 9/2014 | Venkatraman et al. |
| 2016/0091965 A1 | 3/2016 | Wang et al. |

(Continued)

FOREIGN PATENT DOCUMENTS

| | | |
|---|---|---|
| CN | 1111121 A | 11/1995 |
| CN | 105943015 A | 9/2016 |

(Continued)

OTHER PUBLICATIONS

Rong, et al: "Sportive heart ratemeasuring systembased on deep learning", Journal of Electronic Measurement and Instrumentation, vol. 31, No. 12, Dec. 31, 2017, 6 pages.

*Primary Examiner* — Jeffrey G Hoekstra
*Assistant Examiner* — Nicholas A Robinson
(74) *Attorney, Agent, or Firm* — Womble Bond Dickinson (US) LLP

(57) ABSTRACT

This application provides a heart rate detection method and an electronic device. Through the solution, when it is detected that a user wearing a smart wearable device is making a first workout, a PPG signal is acquired through a PPG sensor in the smart wearable device; first heart rate data is obtained based on the PPG signal and a first deep sequence neural network model; second heart rate data is obtained based on the PPG signal and a first frequency tracking algorithm model; and the first heart rate data and the second heart rate data are fused to obtain a target heart rate of the user. Because a frequency tracking algorithm can quickly track a heart rate change, thus the solution can compensate for a scenario in which a deep sequence neural (Continued)

network cannot implement timely tracking in the case of a sudden change of heart rate.

19 Claims, 18 Drawing Sheets

(56) References Cited

U.S. PATENT DOCUMENTS

| | | | |
|---|---|---|---|
| 2018/0249964 A1 | 9/2018 | Qian et al. | |
| 2019/0133468 A1 | 5/2019 | Aliamiri et al. | |
| 2021/0106241 A1 | 4/2021 | Kerman et al. | |

FOREIGN PATENT DOCUMENTS

| | | | |
|---|---|---|---|
| CN | 105997043 A | 10/2016 | |
| CN | 106922185 A | 7/2017 | |
| CN | 108903929 A | 11/2018 | |
| CN | 108926338 A | 12/2018 | |
| CN | 109620262 A | 4/2019 | |
| CN | 109924960 A | 6/2019 | |
| CN | 110151158 A | 8/2019 | |
| CN | 110477895 A | 11/2019 | |
| CN | 110664390 A | 1/2020 | |
| CN | 111481190 A | 8/2020 | |
| CN | 113269301 A | 8/2021 | |
| EP | 3851029 A1 | 7/2021 | |
| KR | 20210066710 A | 6/2021 | |
| KR | 20210097512 A | 8/2021 | |
| WO | 2019191487 A1 | 10/2019 | |
| WO | 2020259264 A1 | 12/2020 | |

| Training scenario | Quantity of samples | Test values without FT features added Average for 5 bpm | Test values with FT features added Average for 5 bpm | Test values after algorithm fusion Average for 5 bpm |
|---|---|---|---|---|
| Category average | 4803 | 0.917528 | 0.925384 | 0.936274 |
| Sample average | | 0.913020 | 0.921530 | 0.932480 |
| | | | ↑ Accuracy of deep model | ↑ Accuracy of deep model |

HEART RATE DETECTION METHOD AND ELECTRONIC DEVICE

CROSS-REFERENCE TO RELATED APPLICATIONS

This application is a national stage of International Application No. PCT/CN2022/115913, filed on Aug. 30, 2022, which claims priority to Chinese Patent Application No. 202111284126.2, filed on Nov. 1, 2021, and Chinese Patent Application No. 202111644631.3, filed on Dec. 29, 2021. The disclosures of each of the aforementioned applications are hereby incorporated by reference in their entireties.

TECHNICAL FIELD

This application relates to the field of communications technologies, and in particular, to a heart rate detection method and an electronic device.

BACKGROUND

Heart rate is a significant indicator for state of health. A conventional measurement method is heart rate analysis based on electrocardiograph (electrocardiograph, ECG), which requires professional equipment and knowledge and therefore cannot meet daily measurement requirements of users. In recent years, with development and maturity of smart wearable devices (such as smart wristband devices), a heart rate detection scheme based on a smart wearable device has become the mainstream.

At present, smart wearable devices can use photoplethysmography (photoplethysmography, PPG) signals to calculate a heart rate. A PPG sensor includes a light emitting diode (light emitting diode, LED) lamp and a photosensor. The LED lamp continuously projects light onto the skin, and the light passes through the skin tissue and is absorbed by the blood flow. At the same time, the photosensor receives reflected light signals. As an intensity of reflected light is related to a blood flow velocity and the blood flow velocity is affected by periodic heart rhythm, a PPG signal can reflect heart rate information.

However, a large amount of noise is introduced due to factors such as ambient light, baseline drift, and workout artifact during acquisition of a PPG heart rate signal, causing signal distortion and low accuracy of heart rate detection.

SUMMARY

In view of the foregoing technical problem, this application provides a heart rate detection method and an electronic device to resolve a problem of low accuracy of heart rate detection caused by signal distortion resulting from a large amount of noise introduced by factors such as ambient light, baseline drift, and workout artifact.

According to a first aspect, this application provides a heart rate detection method, where the method includes:
  determining that a user wearing a smart wearable device is making a first workout, where a photoplethysmography PPG sensor is disposed in the smart wearable device, and the PPG sensor is configured to acquire a PPG signal;
  obtaining first heart rate data based on the PPG signal and a first deep sequence neural network model;
  obtaining second heart rate data based on the PPG signal and a first frequency tracking algorithm model; and
  fusing the first heart rate data and the second heart rate data to obtain a target heart rate of the user during the first workout.

Through the solution of this application, when it is detected that the user wearing the smart wearable device is making the first workout, the PPG signal is acquired through the PPG sensor in the smart wearable device: the first heart rate data is obtained based on the PPG signal and the first deep sequence neural network model: the second heart rate data is obtained based on the PPG signal and the first frequency tracking algorithm model; and the first heart rate data and the second heart rate data are fused to obtain the target heart rate of the user during the first workout. Because the frequency tracking algorithm can quickly track a heart rate change and can compensate for a scenario in which a deep sequence neural network cannot implement timely tracking in the case of a sudden change of heart rate, the solution of this application can improve accuracy of heart rate prediction by fusing heart rate data obtained by different models.

In some possible implementations, the fusing the first heart rate data and the second heart rate data to obtain a target heart rate of the user during the first workout includes:
  performing weighted summation on the first heart rate data and the second heart rate data according to the following equation, to obtain the target heart rate: $Y=w_1x_1+w_2x_2$, where $x_1$ represents the first heart rate data, $w_1$ represents a weight corresponding to the first heart rate data, $x_2$ represents the second heart rate data, and $w_2$ represents a weight corresponding to the second heart rate data.

In some possible implementations, before the performing weighted summation on the first heart rate data and the second heart rate data, the method further includes:
  obtaining first sample data of the first deep sequence neural network and the first frequency tracking algorithm model in different workout scenarios; and
  performing deep learning on the first sample data through a Bayesian algorithm according to the following equation: $Y=w_1x_1+w_2x_2$, to obtain, through training, values of $w_1$ and $w_2$ in different scenarios.

In some possible implementations, $w_1+w_2=1$.

In some possible implementations, before the fusing the first heart rate data and the second heart rate data, the method further includes:
  determining whether the first workout belongs to a first type of workout, where the first type of workout is a type of workout preset based on characteristics of the frequency tracking algorithm model;
  when the first workout belongs to the first type of workout, determining whether a confidence corresponding to the PPG signal is greater than a confidence threshold; and
  when the confidence corresponding to the PPG signal is greater than the confidence threshold, increasing the weight $w_2$ corresponding to the second heart rate data to $w_2'$.

In some possible implementations, the fusing the first heart rate data and the second heart rate data to obtain a target heart rate of the user during the first workout includes:
  when the first workout belongs to the first type of workout, performing weighted summation on the first heart rate data and the second heart rate data according to the following equation, to obtain the target heart rate: $Y=w_1x_1+w_2'x_2$; or
  when the first workout does not belong to the first type of workout, performing weighted summation on the first heart rate data and the second heart rate data according to the following equation, to obtain the target heart rate: $Y=w_1x_1+w_2x_2$.

In some possible implementations, the first type of workout is walking or cycling.

In some possible implementations, before the obtaining first heart rate data based on the PPG signal and a first deep sequence neural network model, the method further includes:

training a deep sequence neural network model based on data features provided by the first frequency tracking algorithm model, to obtain the first deep sequence neural network model, where the data features include PPG dominant data and acceleration ACC dominant data.

In some possible implementations, the method further includes:

obtaining third heart rate data based on the PPG signal and a time domain interval algorithm model; and fusing the first heart rate data, the second heart rate data, and the third heart rate data to obtain the target heart rate of the user during the first workout.

In some possible implementations, the fusing the first heart rate data, the second heart rate data, and the third heart rate data to obtain the target heart rate of the user during the first workout includes:

performing weighted summation on the first heart rate data, the second heart rate data, and the third heart rate data according to the following equation, to obtain the target heart rate: $Y=w_1x_1+w_2x_2+w_3x_3$, where $x_3$ represents the third heart rate data, and $w_3$ represents a weight corresponding to the third heart rate data.

In some possible implementations, before the performing weighted summation on the first heart rate data, the second heart rate data, and the third heart rate data, the method further includes:

obtaining second sample data of the first deep sequence neural network, the first frequency tracking algorithm model, and the time domain interval algorithm model in different workout scenarios; and performing deep learning on the second sample data through a Bayesian algorithm according to the following equation: $Y=w_1x_1+w_2x_2+w_3x_3$, to obtain, through training, values of $w_1$, $w_2$, and $w_3$ in different scenarios.

In some possible implementations, $w_1+w_2+w_3=1$.

In some possible implementations, before the fusing the first heart rate data, the second heart rate data, and the third heart rate data, the method further includes:

determining whether the first workout belongs to a second type of workout, where the second type of workout is a type of workout preset based on characteristics of the time domain interval algorithm model;

when the first workout belongs to the second type of workout, determining whether an autocorrelation coefficient of the PPG time domain signal is greater than a coefficient threshold; and when the autocorrelation coefficient of the PPG time domain signal is greater than the coefficient threshold, increasing the weight $w_3$ corresponding to the third heart rate data to $w_3'$.

In some possible implementations, the fusing the first heart rate data, the second heart rate data, and the third heart rate data to obtain the target heart rate of the user during the first workout includes:

when the first workout belongs to the second type of workout, performing weighted summation according to the following equation, to obtain the target heart rate: $Y=w_1x_1+w_2x_2+w_3'x_3$; or when the first workout does not belong to the second type of workout, performing weighted summation according to the following equation, to obtain the target heart rate:

$$Y = w_1x_1 + w_2x_2 + w_3x_3.$$

In some possible implementations, the second type of workout is reposing or sleeping.

In some possible implementations, before the obtaining first heart rate data based on the PPG signal and a first deep sequence neural network model, the method further includes:

training a deep sequence neural network model based on first data features provided by the first frequency tracking algorithm model and second data features provided by the time domain interval algorithm model, to obtain the first deep sequence neural network model, where the first data features include PPG dominant data and ACC dominant data, and the second data features include interval duration and a quantity of peak points.

In some possible implementations, after the obtaining the target heart rate of the user during the first workout, the method further includes:

displaying the target heart rate and information about the first workout on a screen of the smart wearable device.

In some possible implementations, the method further includes:

obtaining a multi-scenario sample set, where the multi-scenario sample set is a set of data samples detected in a plurality of workout scenarios;

extracting acceleration ACC sample data, photoplethysmography PPG sample data, and heart rate tags from the multi-scenario sample set;

performing training through a deep sequence neural network, with the ACC sample data and the PPG sample data as inputs and the heart rate tags and workout scenario tags as target variables; and obtaining the first deep sequence neural network, where the first deep sequence neural network has functions of scenario recognition and heart rate prediction.

According to a second aspect, this application provides a heart rate detection apparatus based on decision making with AI dual algorithm engines, where the apparatus includes a unit for performing the method in the first aspect. The apparatus may correspondingly perform the method described in the first aspect. For descriptions of the units in the apparatus, refer to the foregoing descriptions of the first aspect. Details are not described herein again for brevity.

The method described in the first aspect may be implemented by hardware, or may be implemented by hardware executing corresponding software. The hardware or software includes one or more modules or units corresponding to the foregoing functions, for example, a processing module or unit, and a display module or unit.

According to a third aspect, this application provides an electronic device, where the electronic device includes a processor, and the processor is coupled to a memory. The memory is configured to store a computer program or instructions, and the processor is configured to execute the computer program or instructions stored in the memory so that the method in the first aspect is performed.

For example, the processor is configured to execute the computer program or instructions stored in the memory, to enable the apparatus to perform the method in the first aspect.

According to a fourth aspect, this application provides a computer-readable storage medium on which a computer program (which may also be referred to as instructions or code) for implementing the method in the first aspect is stored. For example, when the computer program is executed by a computer, the computer is enabled to perform the method in the first aspect.

According to a fifth aspect, this application provides a chip including a processor. The processor is configured to read and execute a computer program stored in a memory, to perform the method in any one of the first aspect or the possible implementations of the first aspect. Optionally, the chip further includes a memory, where the memory is connected to the processor through a circuit or a wire.

According to a sixth aspect, this application provides a chip system including a processor. The processor is configured to read and execute a computer program stored in a memory, to perform the method in any one of the first aspect or the possible implementations of the first aspect. Optionally, the chip system further includes a memory, where the memory is connected to the processor through a circuit or a wire.

According to a seventh aspect, this application provides a computer program product, where the computer program product includes a computer program (which may also be referred to as instructions or code), and when the computer program is executed by a computer, the computer is enabled to implement the method in the first aspect.

It can be understood that for beneficial effects of the second aspect to the seventh aspect, reference may be made to the relevant descriptions in the first aspect. Details are not described herein again.

DESCRIPTION OF EMBODIMENTS

Figure 1:
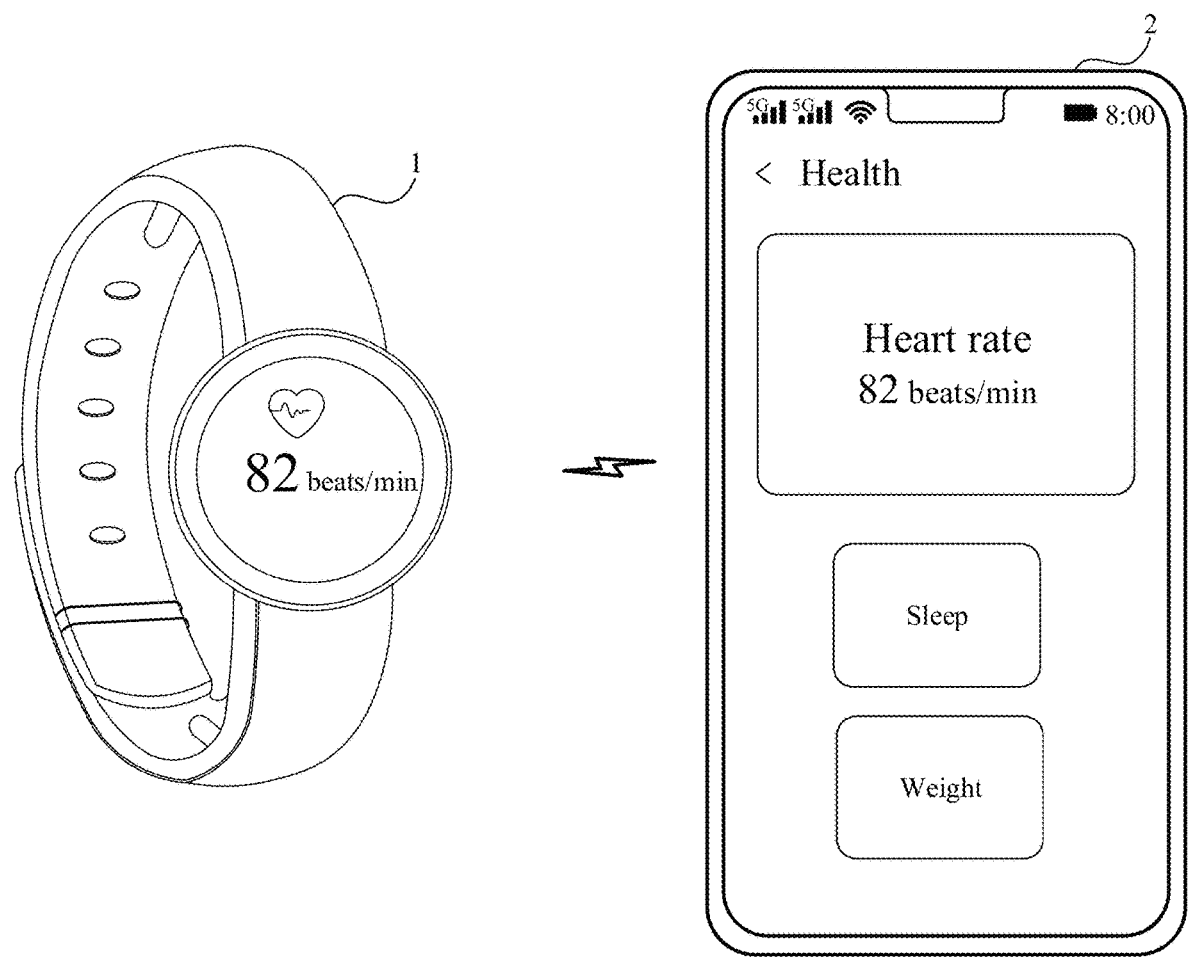
FIG. 1 is a schematic diagram of an application scenario according to an embodiment of this application.

To make the objectives, technical solutions, and advantages of the embodiments of this application clearer, the following clearly and completely describes the technical solutions in the embodiments of this application with reference to the accompanying drawings in the embodiments of this application. Apparently, the embodiments described are some rather than all of the embodiments of this application. All other embodiments obtained by those of ordinary skill in the art based on the embodiments of the present application without creative efforts shall fall within the protection scope of the present application.

The term "and/or" in this specification is an associative relationship for describing associated objects, indicating that three relationships may be present. For example, A and/or B may indicate three cases: presence of only A: presence of both A and B; and presence of only B. A symbol "/" in this specification indicates an "or" relationship between associated objects, for example, A/B indicates A or B.

The terms such as "first" and "second" in the specification and claims of this disclosure are used to distinguish between different objects, but are not used to describe a specific order of the objects. For example, first heart rate data, second heart rate data, and the like are used to differentiate between different heart rate data rather than describe a specific order of heart rate data.

In the embodiments of this application, the word such as "an example" or "for example" is used to represent an example, an instance, or an illustration. Any embodiment or design described by "an example" or "for example" in the embodiments of this application should not be construed as being more preferred or advantageous than other embodiments or designs. To be precise, the word such as "an example" or "for example" is intended to present a related concept in a specific manner.

In the descriptions of the embodiments of this application, unless otherwise stated, "a plurality of" means two or more, for example, a plurality of processing units mean two or more processing units, and a plurality of elements mean two or more elements.

For easy understanding of the embodiments of this application, the following describes some terms used in the embodiments of this application, so as to facilitate understanding of a person skilled in the art.

Photoplethysmography (PPG): PPG is a non-invasive detection technology that uses optical principles to convert a biological signal of human body into an electrical signal. Specifically, light of a light emitting diode (light emitting diode, LED) is projected onto the skin; and a photosensor receives light that is absorbed and then reflected by the skin tissue or that is transmitted through the skin tissue, and converts an electrical signal obtained by the photosensor into a digital signal, that is, a PPG signal. PPG is widely applied in health monitoring of human body such as physiological heart rate, blood oxygen, and pressure due to its non-invasiveness, simplicity, portability and other advantages. Heart rate, as one of the parameters for measuring a heart pulsation capacity, is of medical significance for accurate detection of heart rate.

FIG. 1 is a schematic diagram of a system architecture in each example embodiment of this application. As shown in FIG. 1, the system architecture includes a smart wearable device 1, where the smart wearable device 1 has a PPG sensor. When a user wears the smart wearable device 1 that is on, the smart wearable device 1 can use the PPG technology to detect a heart rate of the user at any moment, and the smart wearable device can display the heart rate. Heart rate, also known quiet heart rate, is a quantity of heartbeats per minute of a normal person in a quiet state, which is generally 60-100 beats per minute (bpm).

It can be understood that the smart wearable device 1 may be an electronic device capable of performing PPG detection on the user, for example, a smart band, a smart watch, glasses, a helmet, a headband, or another wearable electronic device that supports heart rate detection. For ease of illustration, the smart wearable device 1 being a smart watch is used as an example below for description.

Figure 2:
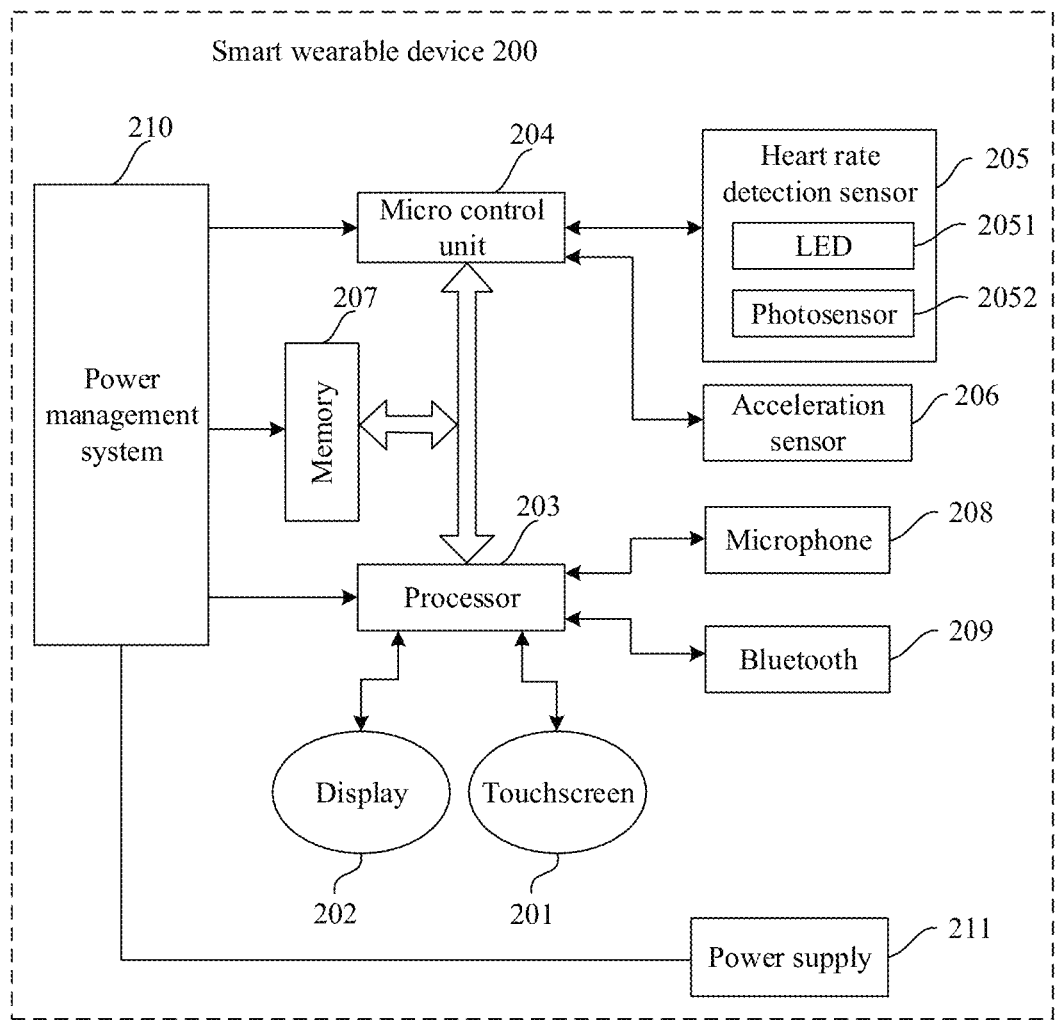
FIG. 2 is a schematic structural diagram of a smart wearable device according to an embodiment of this application.

FIG. 2 is a schematic diagram of a hardware structure of a smart wearable device according to an embodiment of this application. As shown in FIG. 2, the smart wearable device 200 may include a touchscreen 201, a display 202, a processor 203, a micro control unit (micro control unit, MCU) 204, a heart rate detection sensor 205, an acceleration (acceleration, ACC) sensor 206, a memory 207, a microphone (microphone, MIC) 208, a Bluetooth (blue tooth, BT) chip 209, a power management system 210, a power supply 211, and the like. Each of the functional components of the smart watch is described separately below:

The touchscreen 201, also referred to as a touch panel, can collect a touch operation performed by a user wearing the watch on the watch (for example, an operation performed by the user on or near the touch panel by using any proper object or accessory such as a finger or stylus), and drive a corresponding connected apparatus based on a preset program.

The display 202 may be configured to display information input by the user or information provided for the user and various menus of the watch. Further, the touchscreen 201 may cover the display 202. When detecting a touch operation on or near the touchscreen 201, the touchscreen 201 transmits the touch operation to the processor 203 to determine a type of a touch event. Then the processor 203 provides corresponding visual output on the display 202 based on the type of the touch event.

The processor 203 is used for system scheduling, can control the display, the touchscreen, and the MCU 204, and supports control of the microphone 208, the Bluetooth chip 209, and the like. The processor 203 may be connected to the memory 207. The memory 207 may be configured to store program code and data. When running on the smart wearable device 200, the processor 203 may execute computer-executable instructions in the memory 207 to perform operational steps of the method described above.

It should be understood that in the embodiments of this application, the processor 203 may use a central processing unit (central processing unit, CPU). The processor may be a general-purpose processor, a digital signal processor (digital signal processor, DSP), an application-specific integrated circuit (application-specific integrated circuit, ASIC), a field-programmable gate array (field-programmable gate array, FPGA) or another programmable logic device, a discrete gate or transistor logic device, or a discrete hardware component. The general-purpose processor may be a microprocessor, or the processor may be any conventional processor. Alternatively, the processor 203 employs one or more integrated circuits for executing a relevant program to implement technical solutions provided by the embodiments of this application.

The micro control unit 204 is configured to control sensors such as the heart rate detection sensor 205 and the ACC sensor 206, perform calculation on sensor data, and communicate with the processor 203. For example, the micro control unit 204 receives an instruction from the processor 203, or the micro control unit 204 feeds information back to the processor 203.

The micro control unit 204 may be further configured to control lighting on or off of each light source (LED) by controlling a driver of each light source in the heart rate detection sensor 205. The micro control unit 204 may also receive a signal from the heart rate detection sensor 205 and send a signal to the heart rate detection sensor 205.

The heart rate detection sensor 205 may be a PPG sensor, and the PPG sensor can detect a PPG signal, where the PPG signal can reflect heart rate data of the user. The PPG sensor may include a plurality of light sources and photoelectric sensing devices corresponding to the light sources, so as to implement PPG detection. The light source may be a green light source, a red light source, an infrared light source, or the like. For example, the PPG sensor may include an LED 2051 and a photosensor 2052. Specifically, light of the LED 2051 is projected onto the skin; and the photosensor 2052 receives light that is absorbed and then reflected by the skin tissue or that is transmitted through the skin tissue, and converts an electrical signal obtained by the photosensor into a digital signal, that is, a PPG signal. Optionally, the photosensor 2052 may be a photo diode (photo diode, PD) or another photoelectric sensing element.

The ACC sensor 206 is configured to receive a signal sent by the micro control unit 204, and may also send a signal to the micro control unit 204. The signal received by the ACC sensor 206 may include original sensor data and/or filtered or processed sensor data. In the embodiments of this application, the ACC sensor 206 may be configured to detect a workout status of a user, so as to know whether the user wearing the smart wearable electronic device is in a quiet state, and can obtain workout information of the user. A heart rate in the workout status can be detected based on the PPG signal and an ACC signal.

The memory 207 may be configured to store instructions executed by the micro control unit 204 and intermediate data generated during the execution of the instructions, and may be configured to store detection data detected by the PPG sensor, an accelerometer, and the like. In addition, in some embodiments, the memory 105 may be further configured to store correspondences between light source information of each light source and identities of tested users. The light source information may include light intensity and a light intensity sensing range of the light source, and the identities of the tested users may be used to identify different tested users.

In addition, in some embodiments, the memory 207 may further store personal information (such as gender and age) of a tested user that uses the device for the first time, and store atrial fibrillation load data, heart rate, and workout information of a user from the history of the smart wearable device (for example, a smart band). The memory 207 may further store information about a device type.

Optionally, the memory 207 may include a read-only memory and a random access memory; and provides instructions and data for the processor 203. A part of the processor 203 may further include a non-volatile random access memory.

The memory 207 is configured to store a software program and data, and the processor 203 executes various functional applications and data processing of the smart watch by running the software program and data stored in the memory 207.

The microphone 208 is also referred to as a MIC. The microphone 206 can convert an acquired sound signal into an electrical signal which is received and converted into audio data by an audio circuit. The audio circuit may further convert the audio data into an electrical signal and transmit the electrical signal to a speaker, and then the speaker converts the electrical signal into a sound signal for output.

The Bluetooth chip 209 may be used by the smart watch to exchange information with another electronic device (such as a cell phone or a tablet computer), and connects to a server after connecting to a network through the electronic device.

The power supply 211 (for example, a battery) can supply power to all the components. Optionally, the power supply 211 may be logically connected to the processor 203 through the power management system 210, so that functions such as charging and discharging management and power consumption management are implemented by using the power management system 213.

Optionally: the smart wearable device 200 may further include a user interface. The user interface is used for information exchange between the system and a user, so that the user can sign up or login in. The user interface is generally a software interface, which may include a command interface, a program interface, and a graphic interface, that is, software developed on the basis of hardware device interfaces for human-machine communication.

Optionally: the smart wearable device 200 may further include a wireless communication module. The wireless communication module may typically include one or more modules for supporting wireless communication between devices. For example, the wireless communications module may include a wireless fidelity (wireless fidelity. Wi-Fi) module and a near field communication (near field communication, NFC) module.

It should be noted that the hardware function components of the smart wearable device can be changed based on a requirement of the user. It can be understood that the specific embodiment described above is only a specific implementation of this application, and other implementations that can realize the solution of this application also fall within the scope of protection of this application. Details are not described herein.

Optionally, the foregoing system architecture may further include an electronic device 2. The electronic device 2 may establish a wireless connection and perform data communicate with the smart wearable device 1. For example, the smart wearable device 1 can be paired with the electronic device 2 through its own Bluetooth, and perform data communication with the electronic device 2 through a Bluetooth communications link after successful pairing. Certainly, other wireless communications manners may also be used for data communication with a cell phone, for example, radio frequency identification technology and near field communication technology. The electronic device 2 may receive and display a heart rate sent by the smart wearable device 1 for viewing by the user.

It can be understood that the electronic device 2 may include, but is not limited to, a laptop computer, a desktop computer, a tablet computer, a smartphone, a smart wearable device, a head-mounted display, a mobile email device, a portable game console, a portable music player, a reader device, a television with one or more processors embedded or coupled therein, or another electronic device capable of accessing a network. For ease of illustration, the electronic device 2 being a cell phone is used as an example below for description.

A specific process of controlling the PPG sensor to perform PPG measurement in the technical solution of this application is described in detail below.

Figure 3:
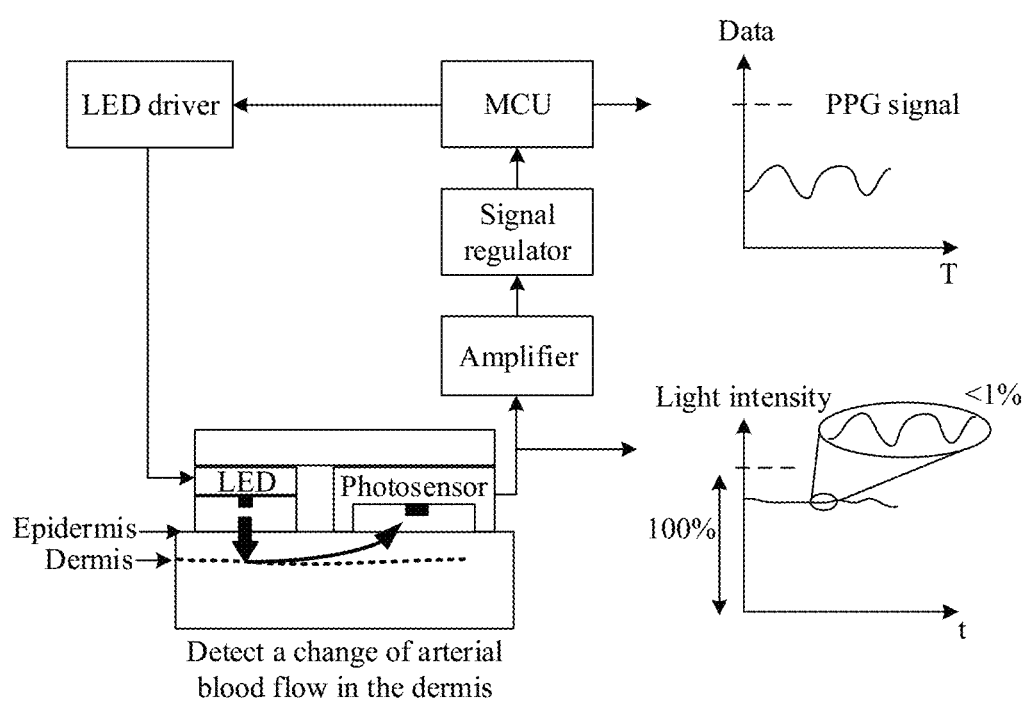
FIG. 3 is a schematic diagram of a PPG heart rate detection principle according to an embodiment of this application.

FIG. 3 is a schematic diagram of a PPG heart rate detection principle. As shown in FIG. 3, the PPG sensor may include an LED lamp and a photosensor. When the PPG sensor is close to or in contact with human skin, the micro control unit invokes an LED driver to trigger the LED lamp to emit light. The LED lamp continuously projects light onto the skin, and the light passes through the skin tissue (including epidermis and dermis) and is absorbed or reflected by the blood flow: The photosensor receives light signals reflected and converts the light signals into electrical signals. In this way an intensity change signal of the reflected light caused by blood flow movement of arteries in the dermis can be detected, as shown in a graph of light intensity data that varies with time t in FIG. 3. The absorption of light by bones, veins and other tissues remains basically unchanged. An intensity of the reflected light is related to a blood flow velocity, and the blood flow velocity is affected by periodic heart rhythm, meaning that an acquired signal is a PPG periodic signal corresponding to the heart rhythm. Therefore, a PPG signal can reflect heart rate information. The PPG signal may also be referred to as a PPG heart rate signal.

Further, the PPG signal may be amplified by an amplifier and has its signal waveform adjusted by a signal adjustment device, and the adjusted PPG signal is sent to the MCU. The MCU processes the adjusted PPG signal to obtain a graph of PPG signal data that varies within a specific time period T shown in FIG. 3.

At present, a large amount of noise may be introduced due to factors such as ambient light, baseline drift, and workout artifact, causing PPG signal distortion.

A smart band being worn may has its position shifted relative to the skin. In this case, the external ambient light may also be acquired during acquisition of the PPG signal. The ambient light as a noise signal affects accuracy of the PPG signal, causing inaccurate heart rate detection.

In addition, baseline drift is noise with a frequency below 1 Hz generated by human breath and relative friction between the skin surface and the PPG sensor. The PPG signal affected by baseline drift may be considered as a combination of a characteristic waveform and a baseline drift signal, and the baseline drift signal can be separated from such PPG signal through appropriate filtering on such PPG signal. An intensity characteristic waveform affected by the baseline drift signal is shown in the dashed box in FIG. 4. Affected by the baseline drift, the intensity characteristic waveform changes relatively slowly, which affects a waveform trend in a long period of time.

Figure 4:
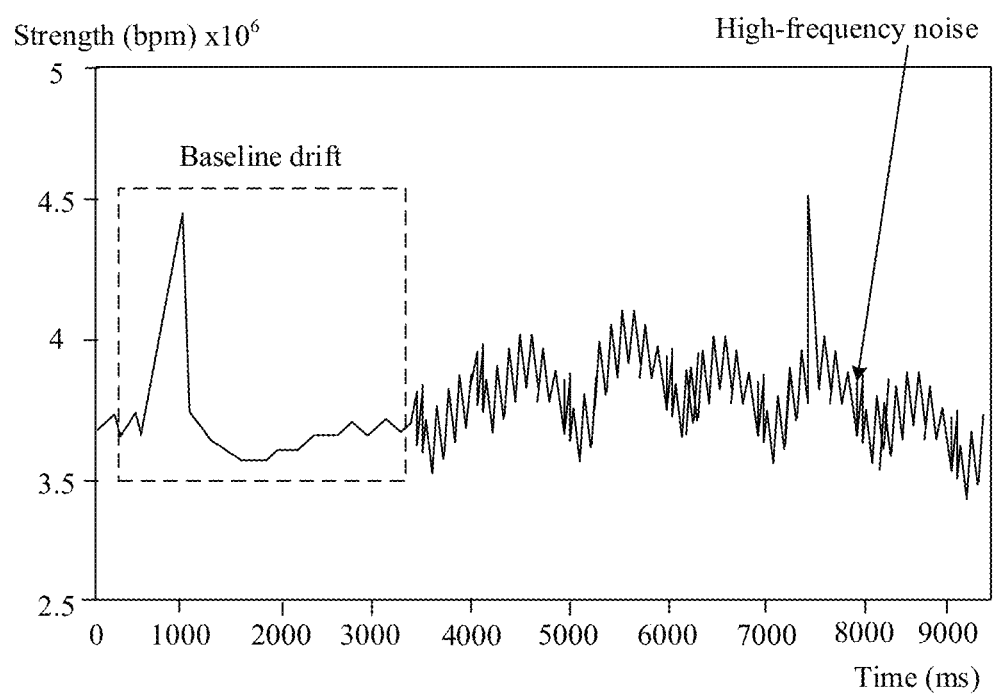
FIG. 4 is a schematic diagram of introduction of a large amount of noise due to factors such as baseline drift and workout artifact according to an embodiment of this application.

Workout artifact is high-frequency noise that occurs when the human body keeps in one kind of irregular workout, such as walking or running. As shown in FIG. 4, high-frequency noise changes relatively quickly and is mixed in a heart rate interval, affecting a waveform change in a short period of time. Workout noise is mixed in a heart rate range in frequency domain and is difficult to distinguish from the heart rate.

Ideally, the PPG signal can accurately detect a heart rate of human body at each moment. However, noise in complex scenarios, such as ambient light, baseline drift, and workout artifact, causes distortion of an actual PPG signal, greatly affecting accuracy of heart rate calculation. The most influential factor is workout artifact. The workout artifact may cause absence or deformation of a crest or a trough of a PPG time domain signal, making a time domain counting method less accurate. The workout artifact also causes an abnormal PPG spectral peak in frequency domain, such that a dominant frequency of the PPG signal at a current moment cannot be accurately located, making it difficult to obtain an accurate result. Therefore, how to adaptively eliminate the complex noise in the PPG signal and improve accuracy of heart rate detection is an important issue.

Figure 5:
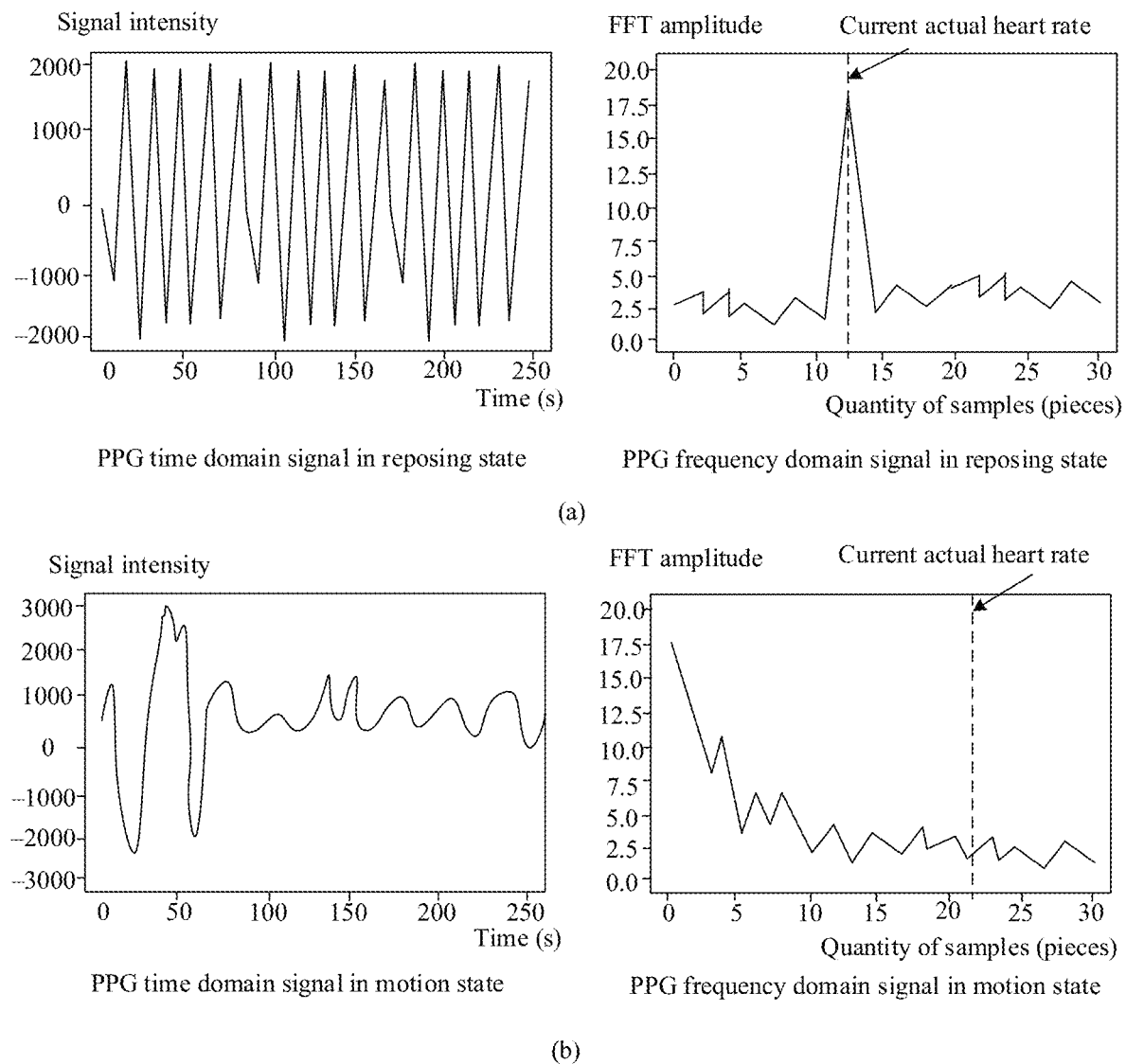
FIG. 5 is a schematic diagram of PPG time domain and frequency domain signals in a reposing state and a workout state according to an embodiment of this application.

The PPG time domain signal and a PPG frequency domain signal in a reposing state are shown in (a) of FIG. 5, and a PPG time domain signal and a PPG frequency domain signal in a workout state are shown in (b) of FIG. 5.

In the graph of PPG time domain signal, the vertical coordinate represents intensity of a PPG signal and the horizontal coordinate represents a sampling time. The graph of PPG time domain signal is a time domain graph after bandpass filtering.

In a spectrum graph of PPG frequency domain signal, the vertical coordinate represents an FFT amplitude and the horizontal coordinate represents a quantity of samples. The spectrum graph of PPG frequency domain signal shows a spectrum after bandpass filtering. The FFT amplitudes represented by the vertical coordinates are normalized, with a value range of [0, 20], The quantity of samples represented by the horizontal coordinate may be 35.

Assuming that a sampling frequency is 25 Hz, accordingly a horizontal coordinate unit interval resolution of the FFT is 25/256=0.097 Hz. It is assumed that a range of FFT horizontal coordinate points in the filtered PPG spectrum graph is [5, 35], Because the horizontal coordinate unit interval resolution of the FFT is 0.097 Hz, a frequency interval corresponding to the range of FFT horizontal coordinate points [5, 35] is [5*0.097 Hz, 35*0.097 Hz], which is approximately [0.5 Hz, 3.5 Hz], The spectrum graph includes spectrum data in a frequency range [0.7 Hz, 3.5 Hz], and frequency domain data obtained at this time is considered as valid spectrum data.

It can be learned from (a) and (b) of FIG. 5 that in the reposing state, the PPG time domain signal is stable and the PPG frequency domain signal has a high energy percentage, so a heart rate can be accurately predicted by using a counting method and a frequency domain peak-finding method. However, in the workout state, the PPG time domain signal has been distorted and the PPG frequency domain signal has an extremely low energy percentage. This is because workout noise is mixed in the heart rate range in frequency domain and is difficult to distinguish from the heart rate. As a result, heart rate prediction is affected. For this reason, a heart rate detection result in the reposing state is relatively accurate. However, a heart rate detection signal in the workout state may be distorted due to interference of high-frequency noise, and consequently a heart rate detected by using a conventional heart rate algorithm is not accurate enough.

In an existing conventional technology, a large amount of artificial noise preprocessing has been performed and rules have been defined for signals, which require a large amount of expertise knowledge as support, and can achieve good results only in specific scenarios with given parameters. The existing technology cannot provide a technical solution to adaptively eliminate noise and compensate for signals under the impact of various complex workout artifacts and noise.

In view of this, this application provides a corresponding solution: enhancing signal quality of a PPG optical path signal source and obtaining a target signal through a high-precision algorithm model to achieve highly accurate prediction.

Figure 6:
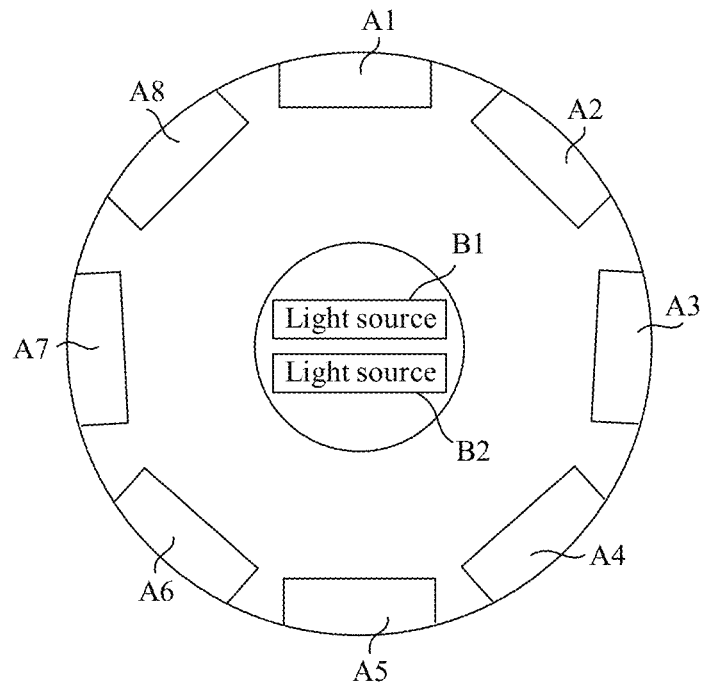
FIG. 6 is a schematic structural diagram of a PPG sensor according to an embodiment of this application.

For example, as shown in FIG. 6, the smart wearable device in the embodiments of this application uses an 8-channel PPG heart rate module. The 8-channel PPG heart rate module includes a total of 8 photosensors: a photosensor A1, a photosensor A2, . . . , and a photosensor A8. These eight photosensors are distributed around one or more light sources. Herein, two light sources. B1 and B2, are used as an example for description. Optionally, the light source B1 may be a green light source and/or a blue light source, and the light source B2 may be a red light source and/or an infrared light source. For example, the light source B1 may be a blue LED and a second light source may be a red LED. In this way, the two light sources project light onto the skin, the light passes through the skin tissue and is absorbed or reflected by the blood flow; and the eight photosensors around the light sources receive reflected light signals and convert the light signals into electrical signals, so that eight PPG signals can be obtained, thereby enhancing the signal quality of the PPG optical path signal source.

The smart wearable device may be a smart watch. With the 8-channel PPG heart rate module, one quality heart rate signal can be obtained through 8-channel data acquisition. 4-channel data processing, and AI fusion, thereby effectively eliminating heart rate signal noise and greatly enhancing an anti-interference capability. Therefore, a risk of unstable heart rate signal can be reduced, and accuracy of dynamic heart rate is improved.

Through the solution of this application, when it is detected that the user wearing the smart wearable device is making the first workout, a PPG signal may be acquired through the PPG sensor in the smart wearable device; the PPG signal is input into a first deep sequence neural network model to obtain first heart rate data; the PPG signal is input into a first frequency tracking algorithm model to obtain second heart rate data; and the first heart rate data and the second heart rate data are fused to obtain a target heart rate of the user during the first workout. Because the frequency tracking algorithm can quickly track a heart rate change and can compensate for a scenario in which the deep sequence neural network cannot implement timely tracking in the case of a sudden change of heart rate, the solution of this application can improve accuracy of heart rate prediction by fusing heart rate data obtained by different models.

A heart rate detection method provided in the embodiments of this application is described as an example below with reference to Embodiment 1 and Embodiment 2.

Embodiment 1

In one solution provided by the embodiment of this application, a heart rate algorithm for a deep sequence neural network and a harmonic frequency tracking (frequency tracking, FT) algorithm can both be used to process PPG signals acquired in different scenarios, so as to enhance signal quality of a PPG optical path signal source. In this way, a target signal can be obtained by using a high-precision algorithm model to achieve highly accurate prediction.

For example, for the 8-channel PPG signals shown in FIG. 6, the heart rate algorithm for the deep sequence neural network and a frequency tracking algorithm may be used to perform AI fusion on a heart rate signal. In this way, the target signal is obtained through the high-precision algorithm model to achieve highly accurate prediction, thereby greatly improving heart rate accuracy.

Figure 7:
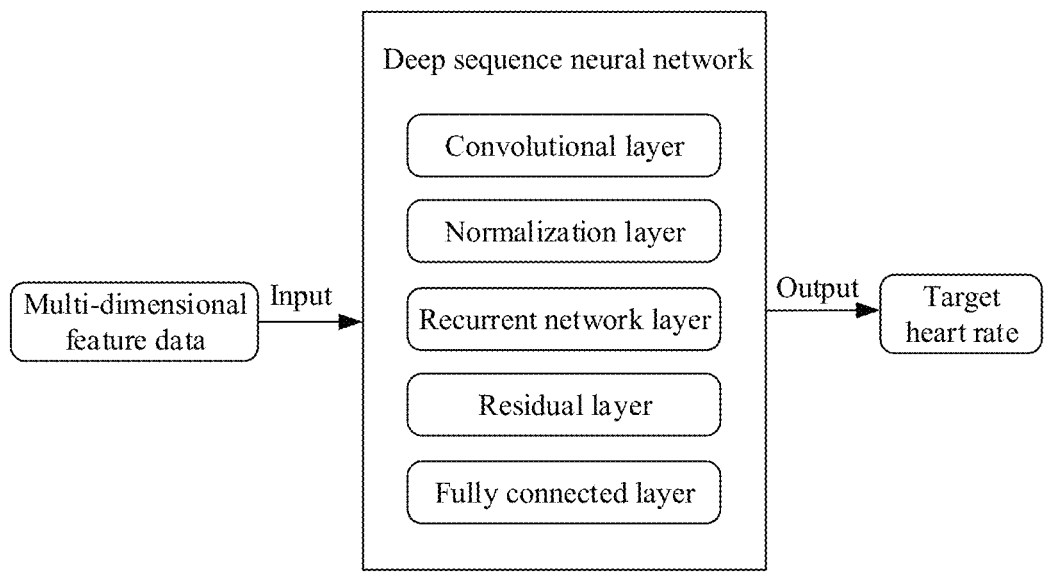
FIG. 7 is a schematic flowchart of a heart rate algorithm for a deep sequence neural network according to an embodiment of this application.

The heart rate algorithm for the deep sequence neural network is described first. FIG. 7 is a structural block diagram of heart rate prediction by using a heart rate algorithm for a deep sequence neural network. As shown in FIG. 7, after multi-dimensional feature data is input into the deep sequence neural network, heart rate prediction is performed by using the heart rate algorithm for the deep sequence neural network, to output a target heart rate. The multi-dimensional feature data may include a PPG time domain signal, an ACC time domain signal, a PPG frequency domain signal, and an ACC frequency domain signal. The deep sequence neural network may include a convolutional layer, a normalization layer, a recurrent network layer, a residual layer, and a fully connected layer. It can be understood that the components of the deep sequence neural network are described as an example herein, and in actual implementation, the deep sequence neural network may include more or fewer components than shown in FIG. 7.

The heart rate algorithm for the deep sequence neural network has the following advantages: First, a heart rate change of human body is highly chronological and non-sudden, and a deep learning model based on time series can effectively build a model based on a change pattern of heart rate. Second, the deep sequence neural network does not require a large amount of expert knowledge to pre-process a large amount of data, but can automatically learn features to implement an end-to-end heart rate monitoring process. Third, a strong anti-interference capability is presented for a case of unstable signals or a sudden change in noise over a short period of time.

However, the heart rate algorithm for the deep sequence neural network also has the following disadvantages: First, timely tracking cannot be implemented in a case of a sudden change in heart rate (for example, a scenario in which a user wearing a smart wearable device gets up quickly). Second, a large amount of training data is required.

Figure 8:
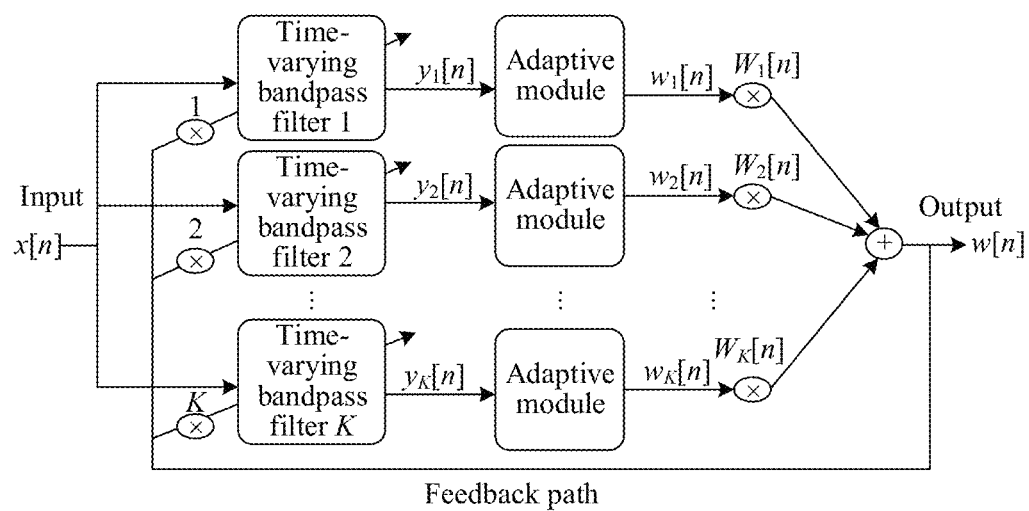
FIG. 8 is a schematic flowchart of a frequency tracking algorithm according to an embodiment of this application.

Next, the harmonic frequency tracking algorithm (which is also referred to as an adaptive filtering algorithm) is described. FIG. 8 is a structural block diagram of a harmonic frequency tracking algorithm. For example, as shown in FIG. 8, a signal $x[n]$ acquired at moment n is input into K time-varying filters to obtain $y_1[n]$, $y_2[n]$, ..., and $y_K[n]$; then, $y_1[n]$, $y_2[n]$, ..., and $y_K[n]$ are input into respective adaptive modules for parameter adjustment to obtain $w_1[n]$, $w_2[n]$, ..., and $w_K[n]$; and, $w_1[n]$, $w_2[n]$, ..., and $w_K[n]$ are multiplied by respective weight parameters $W_1[n]$, $W_2[n]$, ..., and $W_K[n]$ to obtain three products, which are added up to obtain a sum value. Then, this sum value is transmitted through a feedback path as an input of the K time-varying band-pass filters, for cyclically adjusting K coefficients of the filters and finally outputting a target value $w'[n]$.

Such filtering manner is referred to as adaptive filtering. In the adaptive filtering process, without having to know statistical characteristics of the input PPG signal and noise in advance, the filters can learn or estimate the statistical characteristics of the signal during operation and adjust their own parameters based on the statistical characteristics, able to achieve an optimal filtering effect under a specific criterion/cost function. Once the statistical characteristics of the signal change, the filters can track the change and readjust parameters to achieve optimal filtering performance again. Therefore, adaptive filtering is an effective way to process an unstable signal.

The harmonic frequency tracking algorithm has the following advantages: First, the frequency tracking algorithm can quickly track a heart rate change; and second, the harmonic frequency tracking algorithm does not require a large amount of data as support and has a strong mathematical theoretical basis.

However, the harmonic frequency tracking algorithm has the following disadvantages: First, this algorithm requires a large amount of expert knowledge and cannot implement end-to-end heart rate detection; and second, this algorithm is relatively sensitive to noise and has a low anti-interference capability.

Based on the foregoing analysis of the advantages and disadvantages of the heart rate algorithm for the deep sequence neural network and harmonic frequency tracking algorithm, the embodiment of this application proposes that the heart rate algorithm for the deep sequence neural network can be applied in combination with the harmonic frequency tracking algorithm. Specifically, feature fusion and model fusion may be used to deeply integrate the advantages of the two algorithm models in a non-linear manner, and a corresponding algorithm for implementing this is referred to as an artificial intelligence AI fusion algorithm.

It can be learned from experimental data that, the application of the deep sequence neural network in combination with the frequency tracking algorithm in the embodiment of this application can have the following advantages: The frequency tracking algorithm can quickly track a heart rate change, so that the AI fusion algorithm can memorize and learn a trend of heart rate, delivering a strong anti-interference capability and reasoning capability. In addition, the AI fusion algorithm deeply integrates the advantages of the two models in a non-linear manner through feature fusion and model fusion, greatly improving an adaptive capability and detection capability of the algorithm in various scenarios.

Figure 9:
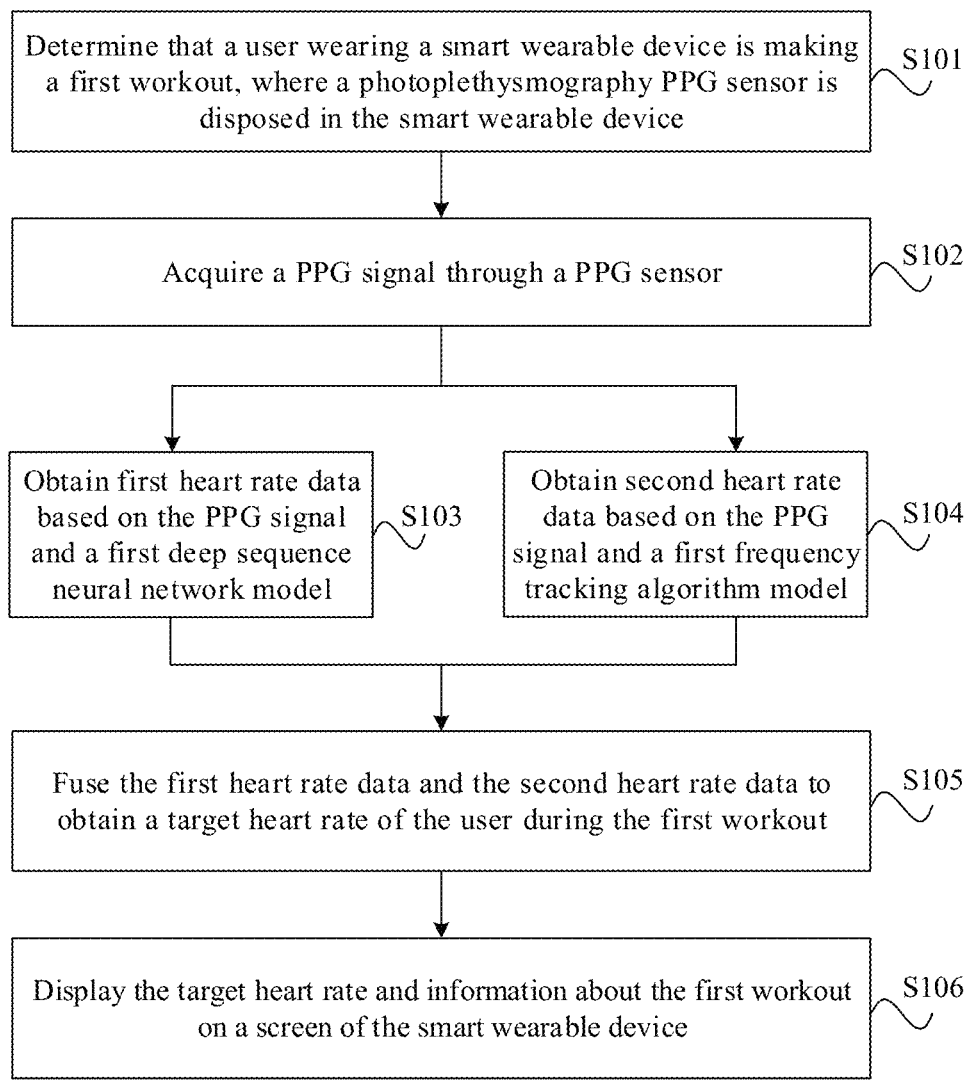
FIG. 9 is a schematic flowchart of a heart rate detection algorithm according to an embodiment of this application.

FIG. 9 is a schematic flowchart of a heart rate detection method according to an embodiment of this application. As shown in FIG. 9, the method includes the following steps S101 to S106.

S101: Determine that a user wearing a smart wearable device is making a first workout, where a photoplethysmography PPG sensor is disposed in the smart wearable device.

For example, the first workout may be walking, running, swimming, cycling, or the like. Cycling may be further classified into indoor cycling and outdoor cycling. Optionally, a first workout scenario may be reposing, sleeping, or the like.

For example, the reposing scenario may be a state when the user is sitting or standing, stationary, or making a slight workout.

S102: Acquire a PPG signal through the PPG sensor.

S103: Obtain first heart rate data based on the PPG signal and a first deep sequence neural network model.

Specifically, the PPG signal may be input into the first deep sequence neural network model to obtain the first heart rate data.

The first deep sequence neural network model is also referred to as a heart rate algorithm for the deep sequence neural network, or deep algorithm or deep learning algorithm for short.

S104: Obtain second heart rate data based on the PPG signal and a first frequency tracking algorithm model.

Specifically, the PPG signal may be input into the first frequency tracking algorithm model to obtain the second heart rate data.

The first frequency tracking algorithm model is a specified frequency tracking algorithm (that is, a harmonic frequency tracking algorithm). For example, the frequency tracking algorithm (referred to as FT algorithm for short) may use an adaptive filtering algorithm, for example, an adaptive filtering algorithm based on the least mean square (least mean square, LMS), or LMS algorithm for short. In the LMS algorithm, a group of weight vectors are found to minimize an expected value of the square of a difference between a predicted output value of samples and an actual output value.

The LMS algorithm uses an adaptive filter to continuously adjust filtering parameters based on previous and current feedback results during filtering. Different parameter update methods bring different results. A filtering parameter update method with a smallest error may be selected, and such parameter update method is referred to as a cost function or an objective function. Because the objective function is to optimize parameter calculation without prior knowledge of a frequency or other characteristics of a signal to be filtered, the objective function can be well applied to PPG signal denoising.

S105: Fuse the first heart rate data and the second heart rate data to obtain a target heart rate of the user in the first workout scenario.

S106: Display the target heart rate and information about the first workout on a screen of the smart wearable device.

It should be noted that an order of performing S103 and S104 is not limited in this embodiment of this application. For example, S103 may be performed before S104, or S104 may be performed before S103, or S103 and S104 may be performed simultaneously. It can be understood that S103 and S104 being performed simultaneously is used as an example for description in FIG. 9.

Data fusion of the heart rate algorithm for the deep sequence neural network and the frequency tracking algorithm are described as an example below: Optionally, in this embodiment of this application, the fusion manners of the deep algorithm and the FT algorithm may include feature fusion, decision fusion, and scenario-based fusion.

First, model training is performed on the deep sequence neural network based on features provided by the FT algorithm and data such as PPG (fusion of multiple features), to obtain an optimized deep sequence neural network.

Then, based on a database of massive samples of different workout scenarios from the optimized deep sequence neural network and the frequency tracking algorithm model, learning is performed on parameters by using a Bayesian algorithm (decision fusion), so as to obtain a weight factor $w_1$ corresponding to the deep algorithm and a weight factor $w_2$ corresponding to the FT algorithm for different scenarios.

Finally, the first heart rate data is obtained based on the PPG signal and the optimized deep sequence neural network; and the second heart rate data is obtained based on the PPG signal and the frequency tracking algorithm model. Weighted fusion is performed on the first heart rate data and the second heart rate data to obtain the target heart rate of the user during the first workout.

The fusion manners for the deep algorithm and the FT algorithm are separately described in detail below.

Manner 1: Feature Fusion

Figure 10:
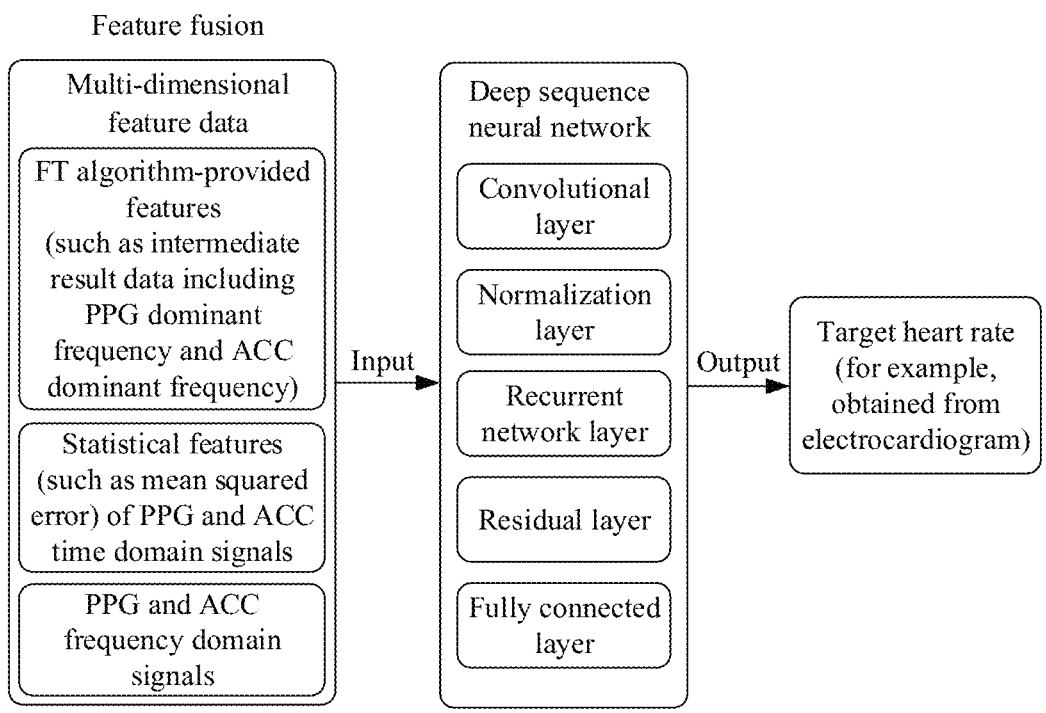
FIG. 10 is a schematic flowchart of feature fusion using a heart rate algorithm for a deep sequence neural network and a frequency tracking algorithm according to an embodiment of this application.

FIG. 10 is a structural block diagram of feature fusion according to Embodiment 1 of this application. As shown in FIG. 10, the multi-dimensional feature data includes statistical features (such as mean squared error) of PPG and ACC time domain signals, PPG and ACC frequency domain signals, and FT algorithm-provided features such as intermediate result data including PPG dominant frequency and ACC dominant frequency. The multi-dimensional feature data is input into the deep sequence neural network, a heart rate obtained from a test such as electrocardiograph (electrocardiograph, ECG) is used as the target heart rate for model training, and parameters are optimized and adjusted to obtain, through training, an optimized deep sequence neural network.

When a preset heart rate detection trigger condition is met, the smart wearable device is triggered to perform heart rate detection and obtain a PPG signal and an ACC signal. For example, the smart wearable device receives a heart rate detection command, and the heart rate detection command triggers the PPG sensor to acquire a PPG signal and triggers an acceleration sensor to acquire an ACC signal, so that the smart wearable device acquires the PPG signal and the ACC signal.

Optionally, in this embodiment of this application, the preset heart rate detection trigger condition may be any one of the following: the smart wearable device has received an operation of triggering enabling of a heart rate detection function by the user, the smart wearable device detects the heart rate in real time, or the smart wearable device detects the heart rate periodically and starts the $N^{th}$ cycle of heart rate detection. This may be specifically determined depending on an actual use requirement, and is not limited in this embodiment of this application.

The FT algorithm-provided features may be intermediate result data including the PPG dominant frequency and ACC dominant frequency obtained by using the harmonic frequency tracking algorithm shown in FIG. 8. It should be noted that the harmonic frequency tracking algorithm shown in FIG. 8 is an example, and in actual implementation, any other frequency tracking algorithm that meets an actual use requirement may be used in this embodiment of this application.

Manner 2: Decision Fusion

Figure 11:
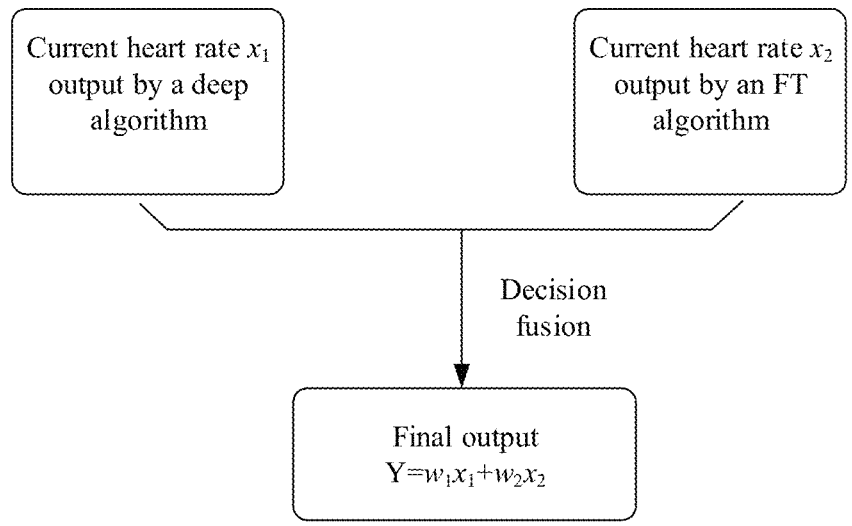
FIG. 11 is a schematic flowchart of decision fusion using a heart rate algorithm for a deep sequence neural network and a frequency tracking algorithm according to an embodiment of this application.

FIG. 11 is a schematic structural block diagram of decision fusion according to Embodiment 1 of this application. As shown in FIG. 11, in this embodiment of this application, assuming that a current heart rate output by the deep algorithm is $x_1$ and a current heart rate output by the FT algorithm is $x_2$, decision fusion may be performed for the deep algorithm and the FT algorithm. In other words, based on a database of massive samples of different workout scenarios obtained by the deep algorithm and the FT algorithm, learning is performed on the parameters by using the Bayesian algorithm, so as to obtain a weight corresponding to the deep algorithm and a weight corresponding to the FT algorithm for different scenarios.

In this embodiment of this application, training is performed according to the following equation (1) and equation (2):

$$Y = w_1 x_1 + w_2 x_2; \quad (1)$$

$$w_1 + w_2 = 1. \quad (2)$$

Y is a heart rate output after training, $w_1$ is a weight factor corresponding to the deep algorithm, and $w_2$ is a weight factor corresponding to the FT algorithm.

It should be noted that different workout scenarios mentioned in this embodiment of this application include, for example, scenarios such as walking, running, and swimming, and certainly, may also include specific scenarios such as reposing and sleeping, which may be specifically determined based on an actual use requirement.

Example data of optimization results in different workout scenarios obtained through training is provided below:

For example, in a sleeping scenario, $w_1=0.20$ and $w_2=0.80$, where the weight factor $w_2$ corresponding to the FT algorithm is greater than the weight factor $w_1$ corresponding to the deep algorithm. In the sleeping scenario, heart rate detection is performed with the FT algorithm as the primary algorithm and the deep algorithm as the secondary.

For example, in a walking scenario, $w_1=0.40$ and $w_2=0.60$, where the weight factor $w_2$ corresponding to the FT algorithm is greater than the weight factor $w_1$ corresponding to the deep algorithm. In the walking scenario, heart rate detection is performed with the FT algorithm as the primary algorithm and the deep algorithm as the secondary.

For example, in a running scenario, $w_1=0.55$ and $w_2=0.45$, where the weight factor $w_1$ corresponding to the deep algorithm is greater than the weight factor $w_2$ corresponding to the FT algorithm. In the running scenario, heart rate detection is performed with the deep algorithm as the primary algorithm and the FT algorithm as the secondary.

For example, in a swimming scenario, $w_1=0.62$ and $w_2=0.38$, where the weight factor $w_1$ corresponding to the deep algorithm is greater than the weight factor $w_2$ corresponding to the FT algorithm. In the swimming scenario, heart rate detection is performed with the deep algorithm as the primary algorithm and the FT algorithm as the secondary.

In this embodiment of this application, in different scenarios, the deep algorithm and the FT algorithm use weight factors corresponding to the scenarios for decision fusion, which can better suppress workout artifact and noise existing in different workout scenarios, and therefore can improve accuracy of heart rate detection.

Manner 3: Scenario-Based Fusion

Figure 12:
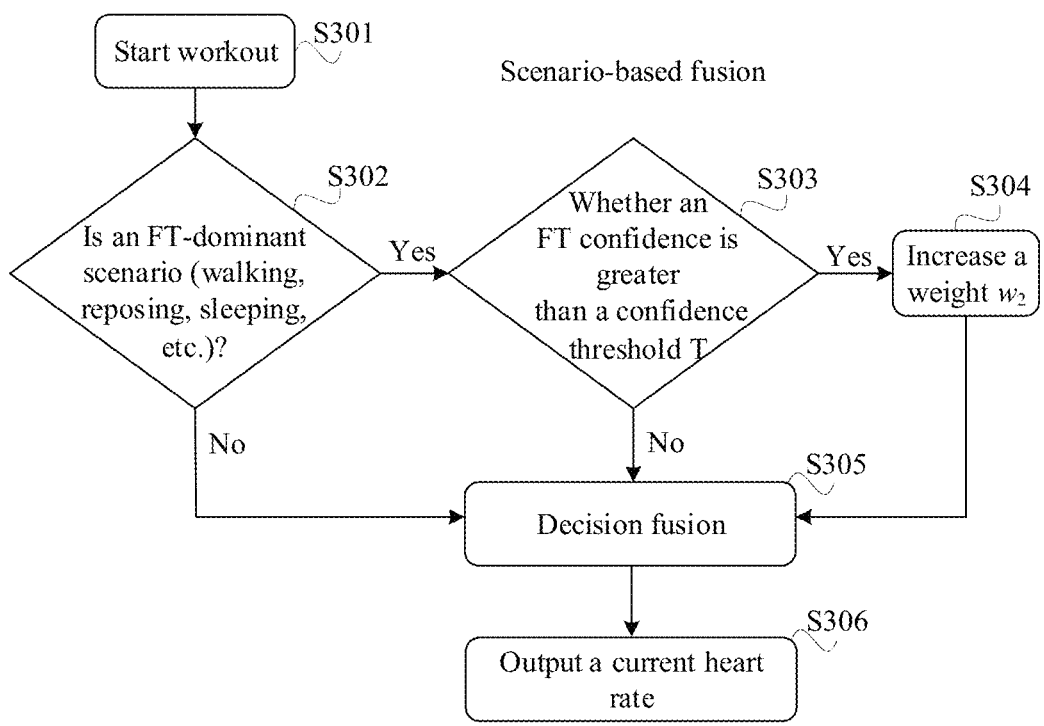
FIG. 12 is a schematic flowchart of scenario-based fusion using a heart rate algorithm for a deep sequence neural network and a frequency tracking algorithm according to an embodiment of this application.

FIG. 12 is a schematic structural block diagram of scenario-based fusion according to Embodiment 1 of this application. As shown in FIG. 12, the scenario-based fusion process may include the following steps S301 to S306.

S301: A smart wearable device detects that a user starts workout.

S302: The smart wearable device determines whether a current scenario is an FT-dominant scenario.

Optionally, the FT-dominant scenario may be a state of walking, reposing, or sleeping. It can be understood that the foregoing scenarios are examples. The specific scenario may be determined depending on an actual use requirement, and is not limited in this embodiment of this application.

If the current scenario is an FT-dominant scenario, the process proceeds to S303. If the current scenario is not an FT-dominant scenario, the process proceeds to S305.

S303: The smart wearable device determines whether an FT confidence is greater than a confidence threshold T.

In this embodiment of this application, if the FT confidence is greater than the confidence threshold T, it indicates that signal quality corresponding to an FT algorithm in the current scenario is good, and a weight of the FT algorithm can be increased to improve accuracy of a fusion algorithm in heart rate detection.

Figure 13:
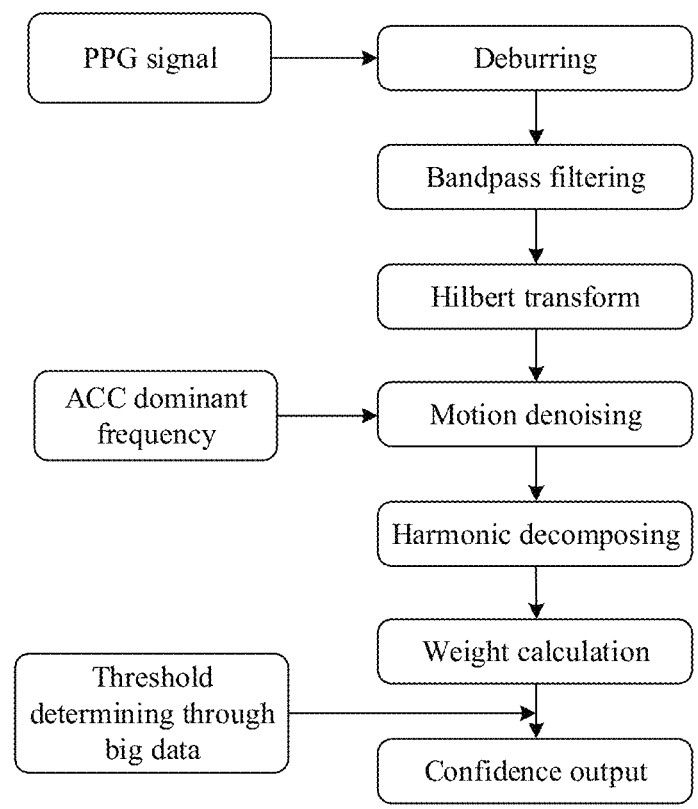
FIG. 13 is a schematic flowchart of determining a confidence based on a PPG signal according to an embodiment of this application.

The following briefly describes how the FT confidence is obtained based on a PPG signal. As shown in FIG. 13, after PPG signal data is acquired, the PPG signal undergoes processing such as deburring and bandpass filtering, and is subjected to Hilbert transform to change the PPG signal into a parsed signal. Then, ACC notch filtering and denoising are performed, that is, an ACC dominant frequency is used to perform notch filtering on the PPG signal, which can eliminate workout noise. The PPG signal may be divided into a plurality of frequency multiplication harmonic signals (that is, harmonic decomposing) by using a plurality of filters. For each harmonic signal, a relative error of the adaptively-filtered PPG signal is solved, so as to obtain a harmonic weight. Through big data analysis, thresholds for all confidence intervals may be determined, so as to obtain a final confidence.

In the process of decomposing harmonics and calculating the weight, the PPG signal may be sent to the plurality of filters to obtain a plurality of harmonics, and a relative error of each signal with respect to an ideal signal is calculated and divided by a sum of the relative errors of all harmonic signals to obtain the harmonic weight.

The threshold for division into confidences may be obtained based on big data statistics. To be specific, a large amount of sample data (for example, more than 10,000 sets of sample data) is acquired, four confidence interval thresholds may be obtained through division according to quartiles, and weights are converted into confidences for output.

If the FT confidence is greater than the confidence threshold T, the process proceeds to S304. If the FT confidence is less than or equal to the confidence threshold T, the process proceeds to S305.

Optionally, other manners such as a neural network model may be used to determine the FT confidence in this embodiment of this application.

S304: The smart wearable device increases the weight factor $w_2$ corresponding to the FT algorithm.

In other words, the weight factor $w_2$ corresponding to the FT algorithm may be increased in a case that the current scenario is an FT-dominant scenario and that the FT confidence is greater than the confidence threshold T.

For example, the weight factor $w_2$ corresponding to the FT algorithm may be increased by multiplying the weight factor $w_2$ corresponding to the FT algorithm by an increment coefficient, so as to increase the weight of the FT algorithm. For easy differentiation, the increased weight factor $w_2$ corresponding to the FT algorithm is denoted as $w_2'$.

Optionally, the foregoing increment coefficient may be 1.1, 1.3, 1.5, or any other value meeting an actual use requirement, which may be specifically determined depending on an actual use requirement, and is not limited in this embodiment of this application.

For example, in the walking scenario, the weight factor $w_1$ corresponding to the deep algorithm is 0.4 and the weight factor $w_2$ corresponding to the FT algorithm is 0.6. After it is determined that the FT confidence is greater than the confidence threshold T, the weight factor $w_2$ corresponding to the FT algorithm may be multiplied by the increment coefficient 1.1, that is, the weight of the FT algorithm is increased, to obtain a corresponding weight factor $w_2'$, 0.66.

S305: The smart wearable device performs decision fusion for the deep algorithm and the FT algorithm.

It should be noted that after S302 or S303, decision fusion is performed in S305 according to $Y=w_1x_1+w_2x_2$, to calculate a heart rate of the user during the current workout.

After S304, decision fusion is performed in S305 according to $Y=w_1x_1+x_2w_2'$, to calculate a heart rate of the user during the current workout.

S306: The smart wearable device outputs a current heart rate obtained through decision fusion.

In this embodiment of this application, dual-algorithm fusion may be performed using the frequency tracking algorithm and the heart rate algorithm for the deep sequence neural network, to obtain an accurate heart rate by segmented synthesis. Taking user behavior or workout states into account, the solution of this application supports detection of heart rates of the user in different workout scenarios (such as various workout states, certainly including a reposing state), and can detect a current scenario and a heart rate in the current scenario. With the solution of this application, continuous real-time heart rate monitoring with high accuracy can be achieved even in the presence of workout noise interference.

Embodiment 2

In another solution provided by the embodiment of this application, PPG signals acquired in different scenarios may be processed by using a heart rate algorithm for a deep sequence neural network, a frequency tracking algorithm, and a time domain interval algorithm together, so as to enhance signal quality of a PPG optical path signal source. In this way, a target signal can be obtained by using a high-precision algorithm model to achieve highly accurate prediction.

The time domain interval algorithm has the following advantages: fast tracking of a trend of heart rate change in the case of little noise, low calculation complexity; and easy implementation. Optionally, the time domain interval algorithm may be a PP interval calculation method, where the PP interval corresponds to a distance between two adjacent P-wave start points displayed on an electrocardiograph.

Similar to the fusion manner described in Embodiment 1 above, the solution provided in Embodiment 2 may also use feature fusion, decision fusion, and scenario-based fusion to perform AI fusion on the heart rate algorithm for the deep sequence neural network, the frequency tracking algorithm, and the time domain interval algorithm.

First, model training is performed on the deep sequence neural network based on time-domain feature data such as FT algorithm-provided features, PP interval duration, and a quantity of peak points, as well as data such as PPG (fusion of multiple features), to obtain an optimized deep sequence neural network.

Then, based on a database of massive samples of different workout scenarios from the optimized deep sequence neural network, the frequency tracking algorithm model, and the time domain interval algorithm, learning is performed on parameters by using a Bayesian algorithm (decision fusion), so as to obtain a weight factor $w_1$ corresponding to the deep algorithm, a weight factor $w_2$ corresponding to the FT algorithm, and $w_3$ corresponding to the time domain interval algorithm for different scenarios.

Finally, first heart rate data is obtained based on a PPG signal and the optimized deep sequence neural network; second heart rate data is obtained based on the PPG signal and the frequency tracking algorithm model; and third heart rate data is obtained based on the PPG signal and the time domain interval algorithm model. Weighted fusion is performed on the first heart rate data, the second heart rate data, and the third heart rate data to obtain the target heart rate of the user during the first workout.

The fusion manners for the deep algorithm, the FT algorithm, and the time domain interval algorithm are separately described in detail below:

Manner 1: Feature Fusion

Figure 14:
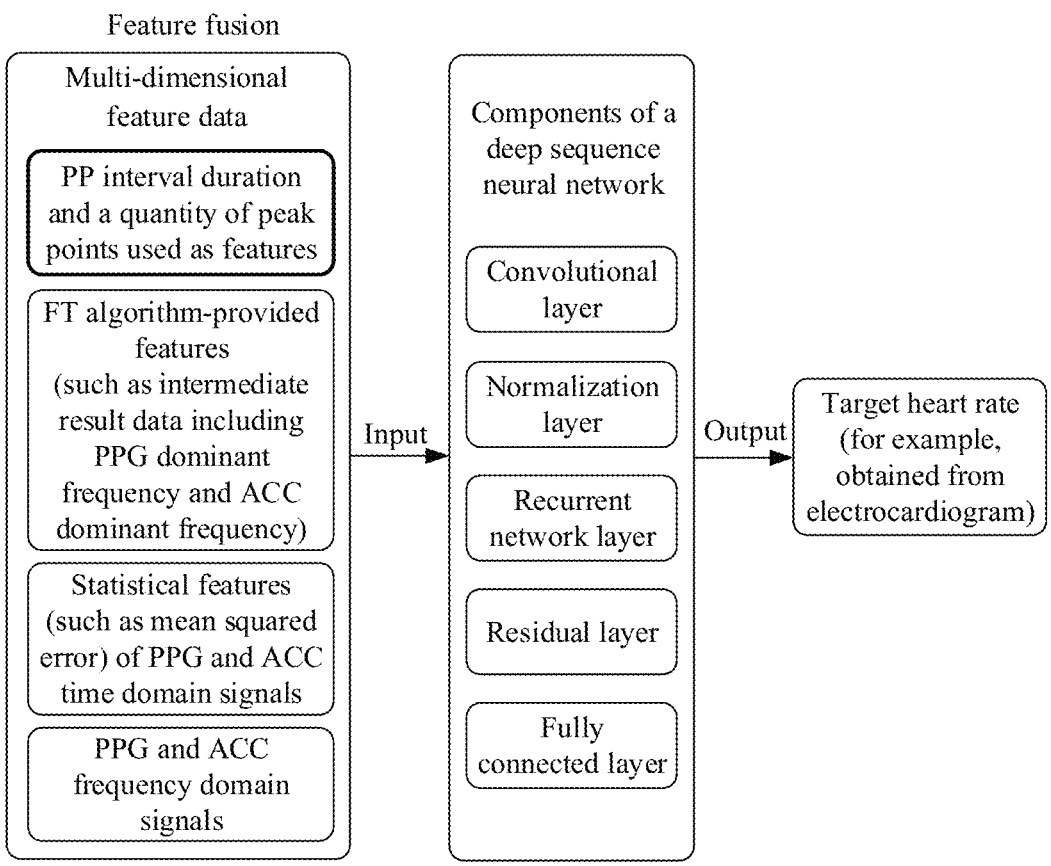
FIG. 14 is a schematic flowchart of feature fusion using a heart rate algorithm for a deep sequence neural network and a frequency tracking algorithm according to another embodiment of this application.

FIG. 14 is a schematic structural block diagram of feature fusion according to Embodiment 2 of this application. As shown in FIG. 14, multi-dimensional feature data includes statistical features (such as mean squared error) of PPG and ACC time domain signals, PPG and ACC frequency domain signals, FT algorithm-provided features (such as intermediate result data including PPG dominant frequency and ACC dominant frequency), and feature data such as the PP interval duration and the quantity of peak points. The multi-dimensional feature data is input into the deep sequence neural network, a heart rate obtained from a test such as electrocardiograph is used as the target heart rate for model training, and parameters are optimized and adjusted to obtain an optimized deep sequence neural network.

Embodiment 2 differs from Embodiment 1 in that Embodiment 2 uses feature data of three algorithms for fusion, which has higher accuracy of heart rate detection.

Manner 2: Decision Fusion

Figure 15:
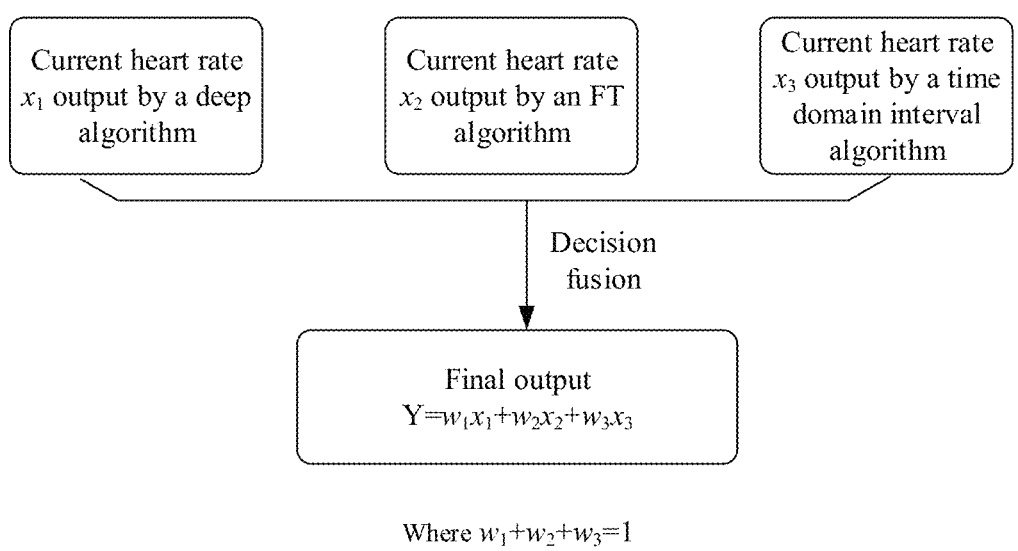
FIG. 15 is a schematic flowchart of decision fusion using a heart rate algorithm for a deep sequence neural network and a frequency tracking algorithm according to another embodiment of this application.

FIG. 15 is a schematic structural block diagram of decision fusion according to Embodiment 1 of this application. As shown in FIG. 15, in this embodiment of this application, assuming that a current heart rate output by the deep algorithm is $x_1$, that a current heart rate output by the FT algorithm is $x_2$, and that a current heart rate output by the time domain interval algorithm is $x_3$, decision fusion may be performed for the deep algorithm and the FT algorithm. In other words, based on a database of massive samples of different workout scenarios obtained through the deep algorithm and the FT algorithm, learning is performed on the parameters by using the Bayesian algorithm, so as to obtain a weight corresponding to the deep algorithm, a weight corresponding to the FT algorithm, and a weight factor corresponding to the time domain interval algorithm for different scenarios.

In this embodiment of this application, training is performed according to the following equation (3) and equation (4):

$$Y = w_1 x_1 + w_2 x_2 + w_3 x_3; \quad (3)$$

$$w_1 + w_2 + w_3 = 1.$$

Y is a heart rate output after training, $w_1$ is a weight factor corresponding to the deep algorithm, $w_2$ is a weight factor corresponding to the FT algorithm, and $w_3$ is the weight factor corresponding to the time domain interval algorithm.

In this embodiment of this application, based on a database of massive samples of different workout scenarios, learning may be performed on the parameters by using the Bayesian algorithm, so that the algorithm weights $w_1$, $w_2$, and $w_3$ for different scenario can be obtained through training. For descriptions of decision fusion in Embodiment 2, refer to the related descriptions of decision fusion in Embodiment 1. Details are not described herein again.

In this embodiment of this application, in different scenarios, the deep algorithm, the FT algorithm, and the time domain interval algorithm use weight factors corresponding to the scenarios for decision fusion, which can better suppress workout artifact and noise existing in different workout scenarios, and therefore can improve accuracy of heart rate detection.

Manner 3: Scenario-Based Fusion

Figure 16:
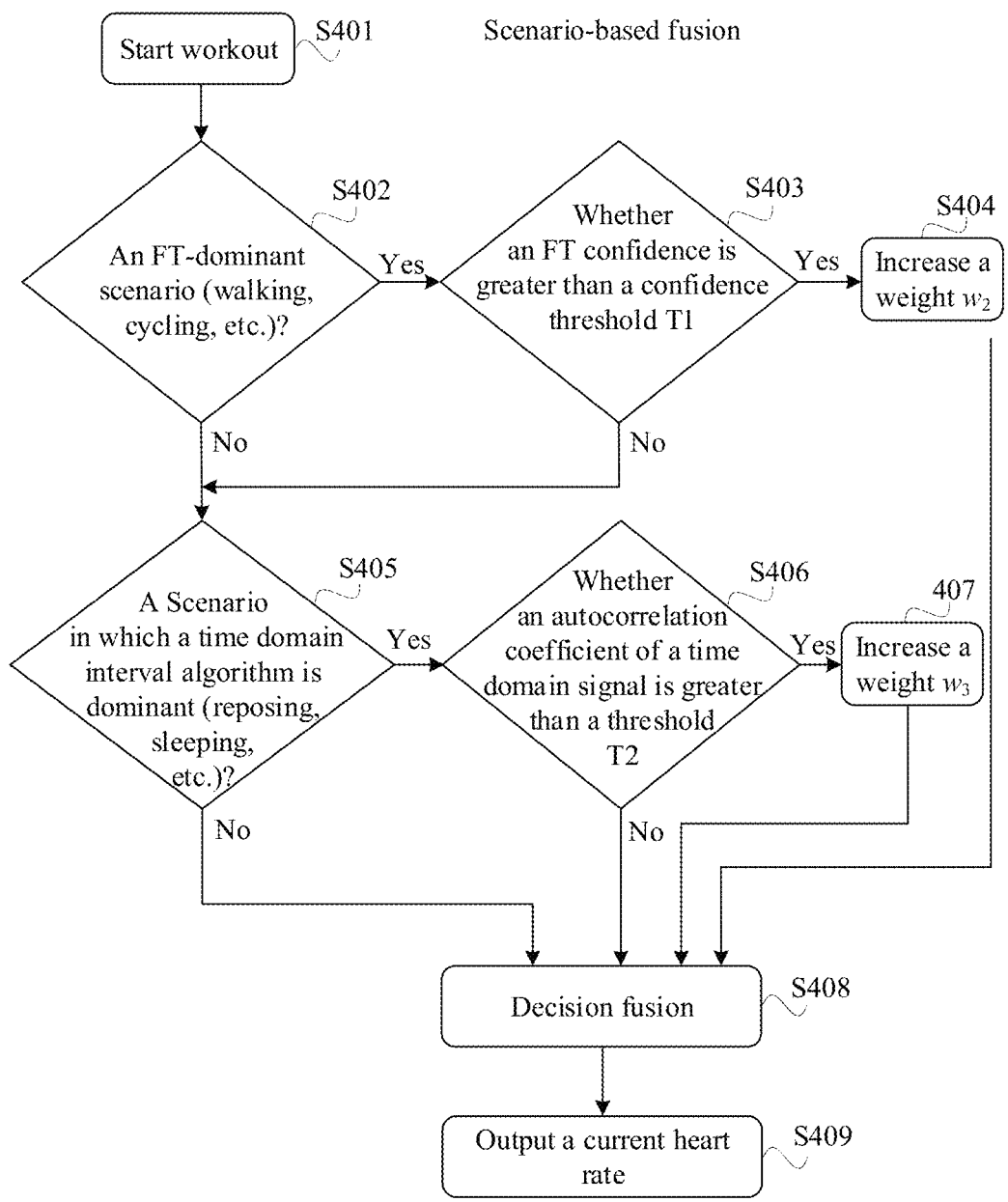
FIG. 16 is a schematic flowchart of scenario-based fusion using a heart rate algorithm for a deep sequence neural network and a frequency tracking algorithm according to another embodiment of this application.

FIG. 16 is a structural block diagram of scenario-based fusion according to Embodiment 2 of this application. As shown in FIG. 16, the scenario-based fusion process may include the following steps S401 to S409.

S401: A smart wearable device detects that a user starts workout.

S402: The smart wearable device determines whether a current scenario is an FT-dominant scenario.

Optionally, the FT-dominant scenario may be a state of walking, cycling, or the like. It can be understood that the foregoing scenarios are examples. The specific scenario may be determined depending on an actual use requirement, and is not limited in this embodiment of this application.

If the current scenario is an FT-dominant scenario, the process proceeds to S403. If the current scenario is not an FT-dominant scenario, the process proceeds to S405.

S403: The smart wearable device determines whether an FT confidence is greater than a confidence threshold T1.

In this embodiment of this application, if the FT confidence is greater than the confidence threshold T1, it indicates that signal quality corresponding to an FT algorithm in the current scenario is good, and a weight of the FT algorithm can be increased to improve accuracy of a fusion algorithm in heart rate detection.

For descriptions of the FT confidence in Embodiment 2, refer to the detailed descriptions of the FT confidence in Embodiment 1. Details are not described herein again.

If the FT confidence is greater than the confidence threshold T1, the process proceeds to S404. If the FT confidence is less than or equal to the confidence threshold T, the process proceeds to S405.

S404: The smart wearable device increases the weight factor $w_2$ corresponding to the FT algorithm.

For example, the weight factor $w_2$ corresponding to the FT algorithm may be increased by multiplying the weight factor $w_2$ corresponding to the FT algorithm by an increment coefficient a, that is, the weight of the FT algorithm is increased. For easy differentiation, the increased weight factor $w_2$ corresponding to the FT algorithm is denoted as $w_2'$.

Optionally, the foregoing increment coefficient a may be 1.1, 1.3, 1.5, or any other value meeting an actual use requirement, which may be specifically determined depending on an actual use requirement, and is not limited in this embodiment of this application.

For example, in a walking scenario, it is assumed that the weight factor $w_1$ corresponding to the deep algorithm is 0.4, that the weight factor $w_2$ corresponding to the FT algorithm is 0.5, and that the weight factor $w_3$ corresponding to the time domain interval algorithm is 0.1. After it is determined that the FT confidence is greater than the confidence threshold T, the weight factor $w_2$ corresponding to the FT algorithm may be multiplied by the increment coefficient 1.3, that is, the weight of the FT algorithm is increased, to obtain a corresponding weight factor $w_2'$, 0.65.

S405: The smart wearable device determines whether a current scenario is a scenario in which the time domain interval algorithm is dominant.

For example, the scenario in which the time domain interval algorithm is dominant may be a state of reposing, sleeping, or the like.

If the current scenario is a scenario in which the time domain interval algorithm is dominant, the process proceeds to S406. If the current scenario is not a scenario in which the time domain interval algorithm is dominant, the process proceeds to S408.

S406: The smart wearable device determines whether an autocorrelation coefficient of a PPG time domain signal is greater than a threshold T2.

The autocorrelation coefficient may be calculated for evaluating a periodicity of a current PPG time domain signal.

It should be noted that the autocorrelation coefficient measures a degree of correlation of a same event in two different periods of time, that is, measures a current effect of past behavior of an object on the object. A larger autocorrelation coefficient indicates a closer correlation.

For example, covariance may be used to describe correlation between two different sequences of a same length. A larger value of covariance indicates a closer correlation between the two sequences.

The threshold T2 may be an autocorrelation coefficient determined based on a large amount of experimental data.

In this embodiment of this application, if an autocorrelation coefficient of a time domain signal is greater than the confidence threshold T2, it indicates that signal quality corresponding to the time domain interval algorithm in the current scenario is good, and a weight of the time domain interval algorithm can be increased to improve accuracy of a fusion algorithm in heart rate detection.

If the autocorrelation coefficient of the time domain signal is greater than the threshold T2, the process proceeds to S407. If the autocorrelation coefficient of the time domain signal is less than or equal to the threshold T2, the process proceeds to S408.

S407: The smart wearable device increases the weight factor $w_3$ corresponding to the time domain interval algorithm.

In other words, the weight factor $w_3$ corresponding to the time domain interval algorithm may be increased in a case that the current scenario is a scenario in which the time domain interval algorithm is dominant and that the autocorrelation coefficient of the time domain signal is greater than the threshold T2.

For example, the weight factor $w_3$ corresponding to the time domain interval algorithm may be increased by multiplying the weight factor $w_3$ corresponding to the time domain interval algorithm by an increment coefficient b, that is, the weight of the time domain interval algorithm is increased. For easy differentiation, the increased weight factor $w_3$ corresponding to the time domain interval algorithm is denoted as $w_3'$.

Optionally, the foregoing increment coefficient b may be 1.1, 1.3, 1.5, or any other value meeting an actual use requirement, which may be specifically determined depending on an actual use requirement, and is not limited in this embodiment of this application.

Optionally, the increment coefficient a and the increment coefficient b may be the same or different. This may be specifically determined depending on an actual use requirement, and is not limited in this embodiment of this application. For example, the increment coefficient a may be 1.3 and the increment coefficient b may be 1.1.

For example, in a sleeping scenario, it is assumed that the weight factor $w_1$ corresponding to the deep algorithm is 0.2, that the weight factor $w_2$ corresponding to the FT algorithm is 0.7, and that the weight factor w's corresponding to the time domain interval algorithm is 0.1. After it is determined that the autocorrelation coefficient of the time domain signal is greater than the threshold T2, the weight factor $w_3$ corresponding to the time domain interval algorithm may be multiplied by the increment coefficient 1.1, that is, the weight of the FT algorithm is increased, to obtain a corresponding weight factor $w_3'$, 0.11.

S408: The smart wearable device performs decision fusion for the deep algorithm, the FT algorithm, and the time domain interval algorithm.

It should be noted that after S405 (with a negative answer) or S406 (with a negative answer), in S408, decision fusion is performed according to $Y=w_1x_1+w_2x_2+w_3x_3$, to calculate a heart rate of the user during the current workout.

After S404, in S408, decision fusion is performed according to $Y=w_1x_1+w_2x_2'+w_3x_3$, to calculate a heart rate of the user during the current workout.

After S407, in S408, decision fusion is performed according to $Y=w_1x_1+x_2w_2+x_3w_3'$, to calculate a heart rate of the user during the current workout.

S409: The smart wearable device outputs a current heart rate obtained through decision fusion.

Taking user behavior or workout states into account, the solution of this application supports detection of heart rates of the user in different workout scenarios (such as various workout states, certainly including a reposing state), and can detect a current scenario and a heart rate in the current scenario. With the solution of this application, continuous real-time heart rate monitoring with high accuracy can be achieved even in the presence of workout noise interference.

It can be learned from experimental data that, the deep sequence neural network is fused with the frequency tracking algorithm in this embodiment of this application, so that advantages of the three algorithm models are deeply integrated in a non-linear manner through feature fusion and model fusion, greatly improving an adaptive capability and detection capability of the algorithm in various scenarios.

Figures 17, 18:
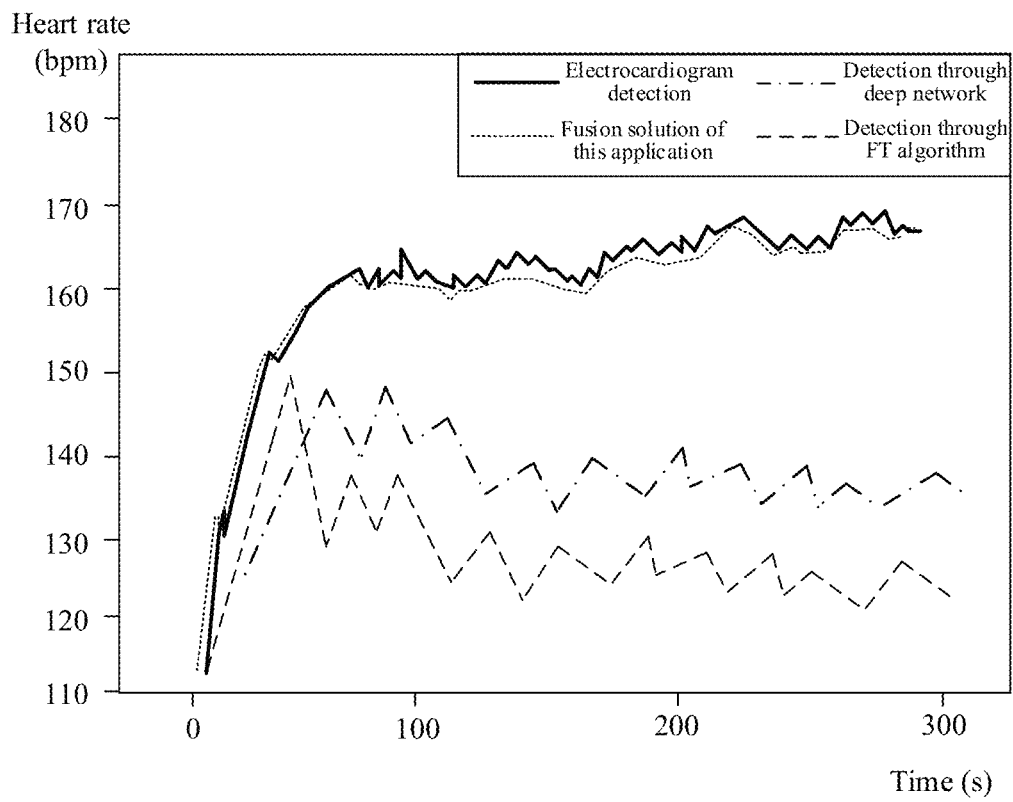
FIG. 17 is a schematic diagram of gains of fusion of a heart rate algorithm for a deep sequence neural network and a frequency tracking algorithm according to an embodiment of this application.
FIG. 18 is a schematic diagram of an effect of applying a fusion solution of this application to a running scenario.

FIG. 17 is a schematic diagram of gains of fusion of a heart rate algorithm for a deep sequence neural network and a frequency tracking algorithm (FT algorithm) according to an embodiment of this application. As shown in FIG. 17, accuracy of a deep model is improved by 1% after intermediate feature data of FT is added, accuracy of the deep model is improved by another 1% after fusion, and a convergence speed of the neural network is correspondingly improved (for example, by 30%).

FIG. 18 is a schematic diagram of an effect of applying a fusion solution of this application to a running scenario. As shown in FIG. 18, the solid line represents a heart rate curve detected by a calibration product (for example, electrocardiograph detection), and the heart rate curve can be used as a standard curve; and the dashed line represents a heart rate curve detected using the solution of this application. It can be learned that the heart rate curve detected using the solution of this application basically fits the standard curve. In other words, accuracy of heart rate detection by the smart wearable devices can be greatly improved by using the solution of this application.

According to a heart rate measurement report given when the technical solution of the embodiments of this application is applied to a walking scenario, comparison between a standard heart rate curve detected using a calibration product 1 (for example, electrocardiogram) and a heart rate curve detected using a product 2 of this application shows that the heart rate curve detected using the product 2 of this application basically fits the standard heart rate curve. In other words, accuracy of heart rate detection by the smart wearable device in the walking scenario can be greatly improved by using the product 2 of this application.

According to a heart rate measurement report given when the solution of the embodiments of this application is applied to a running scenario, comparison between a standard heart rate curve detected using a calibration product 1 (for example, electrocardiogram) and a heart rate curve detected using a product 2 of this application shows that the heart rate curve detected using the product 2 of this application basically fits the standard heart rate curve. In other words, accuracy of heart rate detection by the smart wearable device in the running scenario can be greatly improved by using the product 2 of this application.

For example, the calibration product 1 may be a heart rate chest belt, or certainly may be any other possible heart rate detection apparatus. The heart rate chest belt is a wearable electrocardiograph measurement apparatus. Due to the advantages of small workout amplitude of a measured part, large measurement area, and large correlation between an electrocardiograph signal and heart pulse, the heart rate chest belt is quite accurate in measuring a heart rate and can be used as a calibration or standard product, but a disadvantage of the chest belt is inconvenience of wearing it. The product 2 of this application may be a smart wearable device such as a smart watch or a smart band. This type of device is a measurement apparatus based on photoelectric pulse signals, which is easy to wear and can be closely connected to a device such as a smartphone.

Figure 19:
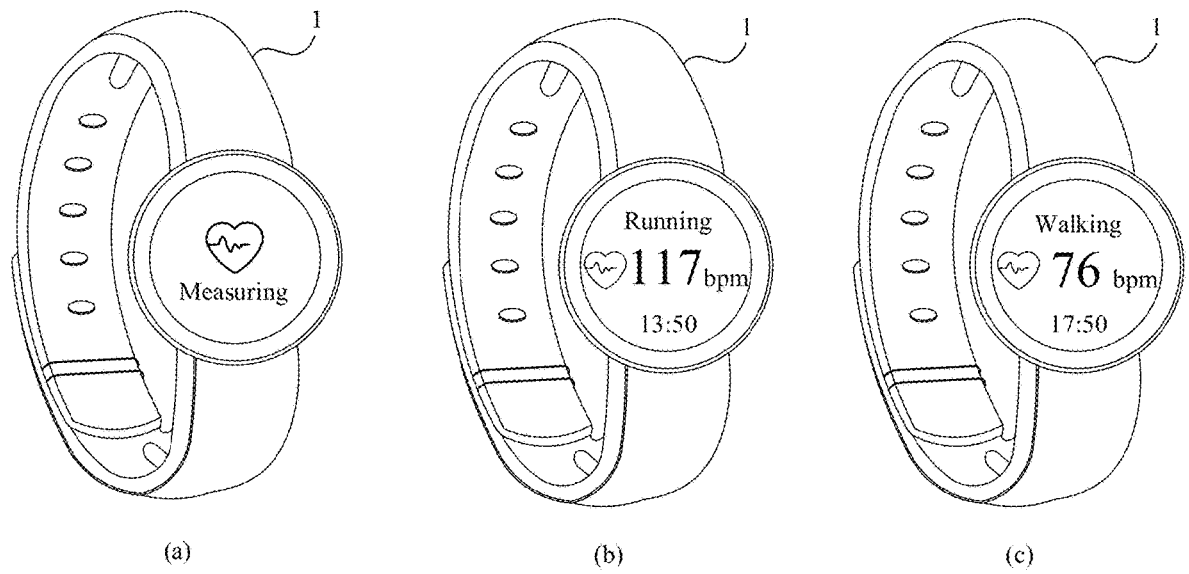
FIG. 19 is a schematic diagram of a user interface when a solution of this application is applied to a smart wearable device.

FIG. 19 is a schematic diagram of a user interface when a solution of this application is applied to a smart wearable device. As shown in (a) in FIG. 19, after a user wears the smart wearable device, the smart wearable device may be triggered to detect a heart rate at any time in different workout scenarios. The heart rate detection may be triggered automatically by a system, or triggered by the user. As shown in (b) in FIG. 19, the smart wearable device displays a result of heart rate detection: in a running scenario, a heart rate of the user is 117 bpm. As shown in (c) in FIG. 19, the smart wearable device displays a result of heart rate detection: in a walking scenario, a heart rate of the user is 76 bpm.

Figure 20:
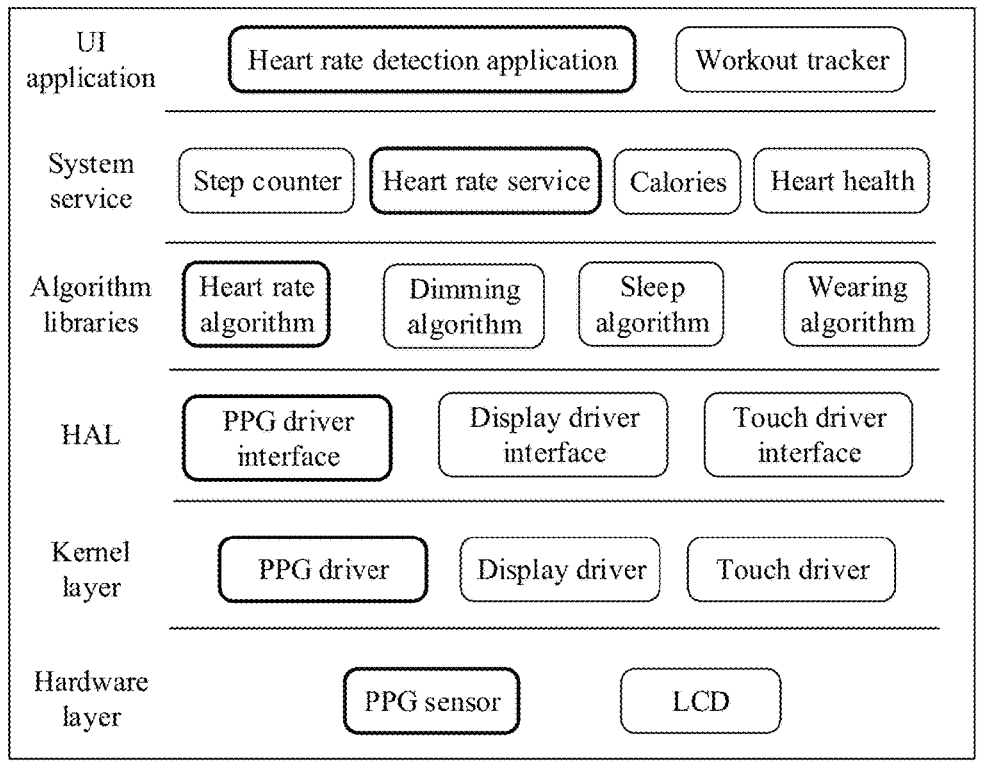
FIG. 20 is a schematic diagram of a software architecture in a technical solution according to an embodiment of this application.

FIG. 20 is a schematic diagram of a software architecture in a technical solution according to an embodiment of this application. As shown in FIG. 20, the software architecture in the solution of this application may include a user interface (user interface. UI) application layer, a system service layer (that is, a framework layer), algorithm libraries, a hardware abstraction layer (hardware abstraction layer. HAL), a kernel layer, and a hardware layer. The UI application layer may include a heart rate detection application, a workout recorder application, and the like. The system service layer may include a step counter service, a heart rate service, a calorie calculation service, a heart health service, and the like. The algorithm libraries may include a heart rate algorithm, a dimming algorithm, a sleep algorithm, a wearing algorithm, and the like. The HAL layer may include a PPG driver interface, a display interface, a touch interface, and the like. The kernel layer may include a PPG driver, a display driver, a touch driver, and the like. The hardware layer may include a PPG sensor, a liquid crystal display (liquid crystal display LCD), a motor, and the like.

The heart rate detection application, the heart rate service, the heart rate algorithm, the PPG driver interface, the PPG driver, and the PPG sensor are used in the solution of this application for heart rate detection. Certainly, a display driver interface, the display driver, and the LCD are also used in the solution of this application for heart rate data display.

It can be understood that the software architecture shown in FIG. 20 is an example. A specific software architecture may be specifically determined depending on an actual use requirement, and is not limited in the embodiments of this application.

In the embodiments of this application, decision fusion is performed on the heart rate prediction algorithms, that is, the frequency tracking algorithm and the deep learning algorithm, to build, through multi-model fusion and an attention Attention mechanism, a dynamic neural network for end-to-end scenario recognition and heart rate prediction, which can improve accuracy of heart rate prediction. In conclusion, the technical solution provided by the embodiments of this application provides a new idea of multi-algorithm decision fusion and proposes three decision fusion methods for the conventional frequency tracking algorithm and the deep learning algorithm, thereby improving accuracy of heart rate detection.

It should also be noted that in the embodiments of this application. "greater than" may be replaced with "greater than or equal to". "less than or equal to" may be replaced with "less than". "greater than or equal to" may be replaced with "greater than", and "less than" may be replaced with "less than or equal to".

The embodiments described in this specification may be independent solutions or may be combined according to inherent logic, all of which fall within the scope of protection of this application.

It can be understood that the methods and operations implemented by the smart wearable device in the foregoing method embodiments may alternatively be implemented by a component (for example, a chip or a circuit) that can be used in the smart wearable device.

The foregoing has described the method embodiments of this application, and the following will describe an apparatus embodiment of this application. It should be understood that descriptions of the apparatus embodiment correspond to the descriptions of the method embodiment, and therefore for content that is not described in detail, refer to the method embodiment. Details are not described herein again for brevity.

The solution provided by the embodiments of this application is described above mainly from the perspective of method steps. It can be understood that, to implement the foregoing functions, the smart wearable device that implements the method includes corresponding hardware structures and/or software modules for performing the functions. A person skilled in the art should be aware that, in combination with the examples described in the embodiments disclosed in this specification, units and algorithm steps may be implemented by using hardware or a combination of hardware and computer software. Whether a function is performed by hardware or hardware driven by computer software depends on particular applications and design constraints of the technical solution. A person skilled in the art may use different methods to implement the described functions for each particular application, but it should not be considered that the implementation goes beyond the scope of protection of this application.

Figure 21:
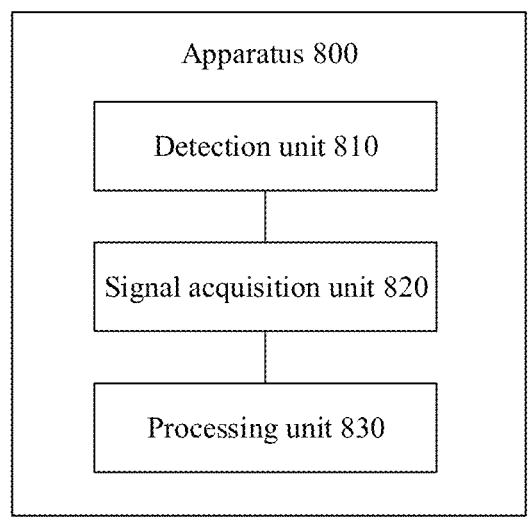
FIG. 21 is a schematic structural diagram of a heart rate detection apparatus according to an embodiment of this application.

In the embodiments of this application, the smart wearable device may be divided into functional modules. For example, the functional modules may be obtained through division based on corresponding functions, or two or more functions may be integrated into one processing module. The integrated module may be implemented in a form of hardware, or may be implemented in a form of a software functional module. It should be noted that, the division into modules in the embodiments of this application is an example, which is merely logical function based division. In actual implementation, another feasible division manner may be used. The functional modules being obtained through division based on corresponding functions are used as an example for description below:

FIG. 21 is a schematic block diagram of a heart rate detection apparatus 800 based on deep learning according to an embodiment of this application. The apparatus 800 may be configured to perform the actions performed by the smart wearable device in the method embodiment. The apparatus 800 includes a detection unit 810, a signal acquisition unit 820, and a processing unit 830.

The detection unit 810 is configured to detect that a user wearing a smart wearable device is making a first workout, where a photoplethysmography PPG sensor is disposed in the smart wearable device.

The signal acquisition unit 820 is configured to acquire a PPG signal through the PPG sensor.

The processing unit 830 is configured to obtain first heart rate data based on the PPG signal and a first deep sequence neural network model; and obtain second heart rate data based on the PPG signal and a first frequency tracking algorithm model.

The processing unit 830 is further configured to fuse the first heart rate data and the second heart rate data to obtain a target heart rate of the user during the first workout.

Through the solution of this application, when it is detected that the user wearing the smart wearable device is making the first workout, a PPG signal may be acquired through the PPG sensor in the smart wearable device: the PPG signal is input into the first deep sequence neural network model to obtain the first heart rate data: the PPG signal is input into the first frequency tracking algorithm model to obtain the second heart rate data; and the first heart rate data and the second heart rate data are fused to obtain the target heart rate of the user in the first workout scenario. Because a frequency tracking algorithm can quickly track a heart rate change and can compensate for a scenario in which the deep sequence neural network cannot implement timely tracking in the case of a sudden change of heart rate, the solution of this application can improve accuracy of heart rate prediction by fusing heart rate data obtained by different models.

In some possible implementations, the processing unit 830 is specifically configured to:
perform weighted summation on the first heart rate data and the second heart rate data according to the following equation, to obtain the target heart rate:

$$Y = w_1 x_1 + w_2 x_2,$$

where
$x_1$ represents the first heart rate data, $w_1$ represents a weight corresponding to the first heart rate data, $x_2$ represents the second heart rate data, and $w_2$ represents a weight corresponding to the second heart rate data.

In some possible implementations, the processing unit 830 is further configured to obtain first sample data of the first deep sequence neural network and the first frequency tracking algorithm model in different workout scenarios; and
perform deep learning on the first sample data through a Bayesian algorithm according to the following equation: $Y=w_1 x_1+w_2 x_2$, to obtain, through training, values of $w_1$ and $w_2$ in different scenarios.

In some possible implementations, $w_1+w_2=1$.

In some possible implementations, the processing unit 830 is further configured to:
determine whether the first workout belongs to a first type of workout, where the first type of workout is a type of workout preset based on characteristics of the frequency tracking algorithm model;
when the first workout belongs to the first type of workout, determine whether a confidence corresponding to the PPG signal is greater than a confidence threshold; and
when the confidence corresponding to the PPG signal is greater than the confidence threshold, increase the weight $w_2$ corresponding to the second heart rate data to $w_2'$.

In some possible implementations, the processing unit 830 is specifically configured to:
when the first workout belongs to the first type of workout, perform weighted summation on the first heart rate data and the second heart rate data according to the following equation, to obtain the target heart rate: $Y=w_1 x_1+w_2' x_2$; or
when the first workout does not belong to the first type of workout, perform weighted summation on the first heart rate data and the second heart rate data according to the following equation, to obtain the target heart rate: $Y=w_1 x_1+w_2 x_2$.

In some possible implementations, the first type of workout is walking or cycling.

In some possible implementations, the processing unit 830 is further configured to:
train a deep sequence neural network model based on data features provided by the first frequency tracking algorithm model, to obtain the first deep sequence neural network model, where
the data features include PPG dominant data and ACC dominant data.

The apparatus 800 in this embodiment of this application may correspondingly perform the method described in the embodiments of this application, and the foregoing and other operations and/or functions of the units in the apparatus 800 are intended to implement corresponding procedures of the method. For brevity, details are not described herein again.

It should be understood that the apparatus 800 in this embodiment of this application may correspond to the smart wearable device 200 in FIG. 2 in the embodiments of this application. The foregoing and other operations and/or functions of the units in the apparatus 800 are intended to implement corresponding procedures of the method. For brevity, details are not described herein again.

Optionally, in some embodiments, an embodiment of this application further provides a computer-readable medium, where the computer-readable medium stores program code. When the computer program code is run on a computer, the computer is enabled to perform the method in the foregoing aspect.

Optionally, in some embodiments, an embodiment of this application further provides a computer program product. The computer program product includes computer program code. When the computer program code is run on a computer, the computer is enabled to perform the method in the foregoing aspect.

In the embodiments of this application, a smart wearable device includes a hardware layer, an operating system layer running over the hardware layer, and an application layer running over the operating system layer. The hardware layer may include hardware such as a central processing unit (central processing unit, CPU), a memory management unit (memory management unit, MMU), and a memory (also referred to as a main memory). The operating system at the operating system layer may be any one or more computer operating systems that implement service processing through processes (process), for example, a Linux operating system, a UNIX operating system, an Android operating system, an iOS operating system, or a Windows operating system. The application layer may include applications such as a browser, an address book, word processing software, and instant messaging software.

The embodiments of this application do not specifically limit a specific structure of an execution body of the method provided in the embodiments of this application, provided that communication can be performed according to the method by running a program having code of the method provided in the embodiments of this application. For example, the execution body of the method provided in the embodiments of this application may be a smart wearable device or a functional module capable of invoking a program and executing the program in the smart wearable device.

The aspects or features of this application may be implemented as methods, apparatuses, or products made by using standard programming and/or engineering technologies. The term "product" used in this specification may cover computer programs that can be accessed by any computer-readable device, carrier, or medium. For example, the computer-readable media may include, but are not limited to: a magnetic storage device (for example, a hard disk, a floppy disk, or a magnetic tape), an optical disk (for example, a compact disc (compact disc, CD), or a digital versatile disc (digital versatile disc, DVD)), a smart card, and a flash memory device (for example, an erasable programmable read-only memory (erasable programmable read-only memory. EPROM), a card, a stick, or a key driver).

Various storage media described in this specification may represent one or more devices and/or other machine-readable media for storing information. The term "machine-readable medium" may include, but is not limited to, wireless channels and various other media capable of storing, containing, and/or carrying instructions and/or data.

It should be understood that the processor mentioned in the embodiments of this application may be a central processing unit (central processing unit, CPU), or may be another general-purpose processor, a digital signal processor (digital signal processor, DSP), an application-specific integrated circuit (application specific integrated circuit, ASIC), a field-programmable gate array (field programmable gate array, FPGA) or another programmable logic device, a discrete gate or a transistor logic device, a discrete hardware component, or the like. The general-purpose processor may be a microprocessor, or the processor may be any conventional processor.

It should be further understood that the memory mentioned in the embodiments of this application may be a volatile memory or a non-volatile memory, or may include both a volatile memory and a non-volatile memory. The non-volatile memory may be a read-only memory (read-only memory, ROM), a programmable read-only memory (programmable ROM, PROM), an erasable programmable read-only memory (erasable PROM, EPROM), an electrically erasable programmable read-only memory (electrically EPROM, EEPROM), or a flash memory. The volatile memory may be a random access memory (random access memory, RAM). For example, the RAM may be used as an external cache. By way of example instead of limitation. RAM may be of a plurality of forms, such as a static random access memory (static RAM. SRAM), a dynamic random access memory (dynamic RAM. DRAM), a synchronous dynamic random access memory (synchronous DRAM, SDRAM), a double data rate synchronous dynamic random access memory (double data rate SDRAM, DDR SDRAM), an enhanced synchronous dynamic random access memory (enhanced SDRAM, ESDRAM), a synchlink dynamic random access memory (synchlink DRAM, SLDRAM), and a direct rambus random access memory (direct rambus RAM, DR RAM).

It should be noted that when the processor is a general-purpose processor, a DSP, an ASIC, an FPGA or another programmable logic device, a discrete gate or a transistor logic device, or a discrete hardware component, a memory (a storage module) may be integrated into the processor.

It should be further noted that the memory described in this specification is intended to include, but is not limited to, these and any other suitable types of memories.

A person of ordinary skill in the art may be aware that, in combination with the examples described in the embodiments disclosed in this specification, units and steps may be implemented by using electronic hardware or a combination of computer software and electronic hardware. Whether the functions are performed by hardware or software depends on particular applications and design constraints of the technical solutions. A person skilled in the art may use different methods to implement the described functions for each particular application, but it should not be considered that the implementation goes beyond the scope of protection of this application.

A person skilled in the art can clearly understand that for convenience and brevity of description, reference may be made to the corresponding processes in the foregoing method embodiments for specific working processes of the system, apparatus, and units described above. Details are not described herein again.

In the several embodiments provided in this application, it should be understood that the disclosed system, apparatus, and method may be implemented in other manners. For example, the described apparatus embodiment is merely an example. For example, the unit division is merely logical function division and may be other division in actual implementation. For example, a plurality of units or components may be combined or integrated into another system, or some features may be omitted or not performed. In addition, the displayed or discussed mutual couplings or direct couplings or communication connections may be implemented by using some interfaces. The indirect couplings or communication connections between the apparatuses or units may be implemented in an electrical form, a mechanical form, or other forms.

The units described as separate parts may or may not be physically separate, and parts displayed as units may or may not be physical units, may be located in one place, or may be distributed on a plurality of network units. Some or all of the units may be selected based on an actual requirement to implement the objectives of the solutions in the embodiments.

In addition, functional units in the embodiments of this application may be integrated into one unit, or each of the units may exist alone physically, or two or more units may be integrated into one unit.

If the function is implemented in a form of a software functional unit and sold or used as an independent product, the function may be stored in a computer-readable storage medium. Based on such an understanding, the technical solutions of this application essentially, or the part contributing to the prior art, or some of the technical solutions may be implemented in a form of a computer software product. The computer software product is stored in a storage medium, and includes several instructions for instructing a computer device (which may be a personal computer, a server, a network device, or the like) to perform all or some of the steps of the methods described in the embodiments of this application. The storage medium may include but is not limited to various mediums, such as a USB flash disk, a removable hard disk, a ROM, a RAM, a magnetic disk, or an optical disc, that can store program code.

Unless otherwise defined, all technical and scientific terms used in this specification shall have the same meanings as commonly understood by a person skilled in the art of this application. The terms used in this specification of this application are merely for the purpose of describing specific embodiments, rather than to limit this application.

Only some specific implementations of this application are described above, and the scope of protection of this application is not limited thereto. Any change or replacement that can be readily figured out by a person skilled in the art within the technical scope disclosed in this application shall fall within the scope of protection of this application. Therefore, the protection scope of this application shall be subject to the protection scope of the claims.

What is claimed is:

1. A heart rate detection method, comprising:
   determining that a user wearing a smart wearable device is making a first workout, wherein a photoplethysmography (PPG) sensor is disposed in the smart wearable device, and the PPG sensor is configured to acquire a PPG signal;
   determining first heart rate data, comprising applying the PPG signal as input into a first deep sequence neural network model;
   determining second heart rate data, comprising applying the PPG signal as input into a first frequency tracking algorithm model; and determining a target heart rate of the user, comprising fusing the first heart rate data and the second heart rate data resulting in the target heart rate of the user during the first workout.

2. The method according to claim 1, wherein the fusing the first heart rate data and the second heart rate data to determine the target heart rate of the user during the first workout comprises:

performing weighted summation on the first heart rate data and the second heart rate data according to the following equation, to determine the target heart rate:

$$Y = w_1 x_1 + w_2 x_2,$$

wherein
Y represents the target heart rate, $x_1$ represents the first heart rate data, $w_1$ represents a weight corresponding to the first heart rate data, $x_2$ represents the second heart rate data, and $w_2$ represents a weight corresponding to the second heart rate data;
wherein $w_1 + w_2 = 1$.

3. The method according to claim 2, wherein before the fusing the first heart rate data and the second heart rate data, the method further comprises:
determining whether the first workout belongs to a first type of workout, wherein the first type of workout comprises walking or cycling;
when the first workout belongs to the first type of workout, determining whether a confidence corresponding to the PPG signal is greater than a confidence threshold; and
when the confidence corresponding to the PPG signal is greater than the confidence threshold, increasing the weight $w_2$ corresponding to the second heart rate data to $w_2'$.

4. The method according to claim 3, wherein the fusing the first heart rate data and the second heart rate data to determine the target heart rate of the user during the first workout comprises:
when the first workout belongs to the first type of workout, performing weighted summation on the first heart rate data and the second heart rate data according to the following equation, to determine the target heart rate: $Y = w_1 x_1 + w_2' x_2$; or
when the first workout does not belong to the first type of workout, performing weighted summation on the first heart rate data and the second heart rate data according to the following equation, to determine the target heart rate: $Y = w_1 x_1 + w_2 x_2$.

5. The method according to claim 2, wherein the method further comprises:
determining third heart rate data, comprising applying the PPG signal as input into a time domain interval algorithm model; and
fusing the first heart rate data, the second heart rate data, and the third heart rate data to determine the target heart rate of the user during the first workout.

6. The method according to claim 5, wherein the fusing the first heart rate data, the second heart rate data, and the third heart rate data to determine the target heart rate of the user during the first workout comprises:
performing weighted summation on the first heart rate data, the second heart rate data, and the third heart rate data according to the following equation, to determine the target heart rate:

$$Y = w_1 x_1 + w_2 x_2 + w_3 x_3,$$

wherein
$x_3$ represents the third heart rate data, and $w_3$ represents a weight corresponding to the third heart rate data; wherein $w_1 + w_2 + w_3 = 1$.

7. The method according to claim 5, wherein before the fusing the first heart rate data, the second heart rate data, and the third heart rate data, the method further comprises:
determining whether the first workout belongs to a second type of workout, wherein the second type of workout comprises reposing or sleeping;
when the first workout belongs to the second type of workout, determining whether an autocorrelation coefficient of the PPG time domain signal is greater than a coefficient threshold; and
when the autocorrelation coefficient of the PPG time domain signal is greater than the coefficient threshold, increasing the weight $w_3$ corresponding to the third heart rate data to $w_3'$.

8. The method according to claim 1, wherein after the determining of the target heart rate of the user during the first workout, the method further comprises:
displaying the target heart rate and information about the first workout on a screen of the smart wearable device.

9. The method according to claim 1, wherein the method further comprises:
obtaining a multi-scenario sample set, wherein the multi-scenario sample set is a set of data samples detected in a plurality of workout scenarios;
extracting acceleration sample data, PPG sample data, and heart rate tags from the multi-scenario sample set;
performing training through a deep sequence neural network, with the acceleration sample data and the PPG sample data as inputs and the heart rate tags and workout scenario tags as target variables, resulting in the first deep sequence neural network, wherein the first deep sequence neural network has functions of scenario recognition and heart rate prediction.

10. An electronic device, comprising a processor, wherein the processor is coupled to a memory, and the processor is configured to execute a computer program or instructions stored in the memory, to cause the electronic device to implement the following operations:
determining that a user wearing a smart wearable device is making a first workout, wherein a photoplethysmography (PPG) sensor is disposed in the smart wearable device, and the PPG sensor is configured to acquire a PPG signal;
determining first heart rate data, comprising applying the PPG signal as input into a first deep sequence neural network model;
determining second heart rate data, comprising applying the PPG signal as input into a first frequency tracking algorithm model; and
determining a target heart rate of the user, comprising fusing the first heart rate data and the second heart rate data resulting in the target heart rate of the user during the first workout.

11. The electronic device according to claim 10, wherein the fusing the first heart rate data and the second heart rate data to determine the target heart rate of the user during the first workout comprises:

performing weighted summation on the first heart rate data and the second heart rate data according to the following equation, to determine the target heart rate:

$$Y = w_1 x_1 + w_2 x_2,$$

Y represents the target heart rate, $x_1$ represents the first heart rate data, $w_1$ represents a weight corresponding to the first heart rate data, $x_2$ represents the second heart rate data, and $w_2$ represents a weight corresponding to the second heart rate data;
wherein $$w_1 + w_2 = 1.$$

12. The electronic device according to claim 11, wherein before the fusing the first heart rate data and the second heart rate data, the operations further comprise:
  determining whether the first workout belongs to a first type of workout, wherein the first type of workout comprises walking or cycling;
  when the first workout belongs to the first type of workout, determining whether a confidence corresponding to the PPG signal is greater than a confidence threshold; and
  when the confidence corresponding to the PPG signal is greater than the confidence threshold, increasing the weight $w_2$ corresponding to the second heart rate data to $w_2'$.

13. The electronic device according to claim 12, wherein the fusing the first heart rate data and the second heart rate data to determine the target heart rate of the user during the first workout comprises:
  when the first workout belongs to the first type of workout, performing weighted summation on the first heart rate data and the second heart rate data according to the following equation, to determine the target heart rate: $Y=w_1 x_1 + w_2' x_2$; or
  when the first workout does not belong to the first type of workout, performing weighted summation on the first heart rate data and the second heart rate data according to the following equation, to result in the target heart rate: $Y=w_1 x_1 + w_2 x_2$.

14. The electronic device according to claim 11, wherein the operations further comprise:
  determining a third heart rate data, comprising applying the PPG signal as input into a time domain interval algorithm model;
  wherein the determining of the target heart rate, comprising: fusing the first heart rate data, the second heart rate data, and the third heart rate data resulting in the target heart rate of the user during the first workout.

15. The electronic device according to claim 14, wherein the fusing the first heart rate data, the second heart rate data, and the third heart rate data to determine the target heart rate of the user during the first workout comprises:
  performing weighted summation on the first heart rate data, the second heart rate data, and the third heart rate data according to the following equation, to determine the target heart rate:

$$Y = w_1 x_1 + w_2 x_2 + w_3 x_3,$$

wherein
  $x_3$ represents the third heart rate data, and $w_3$ represents a weight corresponding to the third heart rate data; wherein $w_1 + w_2 + w_3 = w_1$.

16. The electronic device according to claim 14, wherein before the fusing the first heart rate data, the second heart rate data, and the third heart rate data, the operations further comprise:
  determining whether the first workout belongs to a second type of workout, wherein the second type of workout comprises reposing or sleeping;
  when the first workout belongs to the second type of workout, determining whether an autocorrelation coefficient of the PPG time domain signal is greater than a coefficient threshold; and
  when the autocorrelation coefficient of the PPG time domain signal is greater than the coefficient threshold, increasing the weight $w_3$ corresponding to the third heart rate data to $w_3'$.

17. The electronic device according to claim 10, wherein after the determining of the target heart rate of the user during the first workout, the operations further comprise:
  displaying the target heart rate and information about the first workout on a screen of the smart wearable device.

18. The electronic device according to claim 10, wherein the operations further comprise:
  obtaining a multi-scenario sample set, wherein the multi-scenario sample set is a set of data samples detected in a plurality of workout scenarios;
  extracting acceleration sample data, PPG sample data, and heart rate tags from the multi-scenario sample set;
  performing training through a deep sequence neural network, with the acceleration sample data and the PPG sample data as inputs and the heart rate tags and workout scenario tags as target variables resulting in the first deep sequence neural network, wherein the first deep sequence neural network has functions of scenario recognition and heart rate prediction.

19. A non-transitory computer-readable storage medium, wherein the non-transitory computer-readable storage medium stores a computer program, and when the computer program is run on an electronic device, the electronic device is to perform the following operations:
  determining that a user wearing a smart wearable device is making a first workout, wherein a photoplethysmography (PPG) sensor is disposed in the smart wearable device, and the PPG sensor is configured to acquire a PPG signal;
  determining first heart rate data, comprising applying the PPG signal as input into a first deep sequence neural network model;
  determining second heart rate data, comprising applying the PPG signal as input into a first frequency tracking algorithm model; and
  determining a target heart rate of the user, comprising fusing the first heart rate data and the second heart rate data resulting in the target heart rate of the user during the first workout.

* * * * *